United States Patent
Specht et al.

(10) Patent No.: US 11,998,395 B2
(45) Date of Patent: *Jun. 4, 2024

(54) POINT SOURCE TRANSMISSION AND SPEED-OF-SOUND CORRECTION USING MULTI-APERTURE ULTRASOUND IMAGING

(71) Applicant: Maui Imaging, Inc., San Jose, CA (US)

(72) Inventors: Donald F. Specht, Los Altos, CA (US); Kenneth D. Brewer, Santa Clara, CA (US)

(73) Assignee: Maui Imaging, Inc., San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/936,420

(22) Filed: Sep. 29, 2022

(65) Prior Publication Data

US 2023/0270416 A1  Aug. 31, 2023

Related U.S. Application Data

(63) Continuation of application No. 16/506,570, filed on Jul. 9, 2019, now Pat. No. 11,464,492, which is a (Continued)

(51) Int. Cl.
*A61B 8/08* (2006.01)
*A61B 8/00* (2006.01)
(Continued)

(52) U.S. Cl.
CPC ............. *A61B 8/5246* (2013.01); *A61B 8/14* (2013.01); *A61B 8/145* (2013.01); *A61B 8/4444* (2013.01);
(Continued)

(58) Field of Classification Search
CPC ......... A61B 8/5246; A61B 8/14; A61B 8/145; A61B 8/4444; A61B 8/4455;
(Continued)

(56) References Cited

U.S. PATENT DOCUMENTS 3,174,286 A  3/1965 Erickson
3,895,381 A  7/1975 Kock
(Continued)

FOREIGN PATENT DOCUMENTS

CN  1535243 A  10/2004
CN  1636150 A  7/2005
(Continued)

OTHER PUBLICATIONS

Abeysekera et al.; Alignment and calibration of dual ultrasound transducers using a wedge phantom; Ultrasound in Medicine and Biology; 37(2); pp. 271-279; Feb. 2011.
(Continued)

*Primary Examiner* — Sanjay Cattungal
(74) *Attorney, Agent, or Firm* — Shay Glenn LLP

(57) ABSTRACT

A Multiple Aperture Ultrasound Imaging system and methods of use are provided with any number of features. In some embodiments, a multi-aperture ultrasound imaging system is configured to transmit and receive ultrasound energy to and from separate physical ultrasound apertures. In some embodiments, a transmit aperture of a multi-aperture ultrasound imaging system is configured to transmit an omni-directional unfocused ultrasound waveform approximating a first point source through a target region. In some embodiments, the ultrasound energy is received with a single receiving aperture. In other embodiments, the ultrasound energy is received with multiple receiving apertures. Algorithms are described that can combine echoes received by one or more receiving apertures to form high resolution (Continued)

ultrasound images. Additional algorithms can solve for variations in tissue speed of sound, thus allowing the ultrasound system to be used virtually anywhere in or on the body.

5 Claims, 7 Drawing Sheets

Related U.S. Application Data continuation of application No. 16/000,507, filed on Jun. 5, 2018, now Pat. No. 10,342,518, which is a continuation of application No. 15/364,075, filed on Nov. 29, 2016, now Pat. No. 9,986,975, which is a continuation of application No. 14/846,374, filed on Sep. 4, 2015, now Pat. No. 9,526,475, which is a continuation of application No. 13/029,907, filed on Feb. 17, 2011, now Pat. No. 9,146,313.

(60) Provisional application No. 61/305,784, filed on Feb. 18, 2010.

(51) Int. Cl.
*A61B 8/14* (2006.01)
*G01S 7/52* (2006.01)
*G01S 15/89* (2006.01)

(52) U.S. Cl.
CPC .......... *A61B 8/4455* (2013.01); *A61B 8/4477* (2013.01); *A61B 8/4483* (2013.01); *A61B 8/463* (2013.01); *A61B 8/5207* (2013.01); *A61B 8/5269* (2013.01); *G01S 7/52049* (2013.01); *G01S 15/8913* (2013.01); *G01S 15/8927* (2013.01); *G01S 15/8961* (2013.01); *G01S 15/8977* (2013.01); *G01S 15/8993* (2013.01); *G01S 15/8997* (2013.01)

(58) Field of Classification Search
CPC ..... A61B 8/4477; A61B 8/4483; A61B 8/463; A61B 8/5207; A61B 8/5269; G01S 7/52049; G01S 15/8913; G01S 15/8927; G01S 15/8961; G01S 15/8977; G01S 15/8993; G01S 15/8997
See application file for complete search history.

(56) References Cited

U.S. PATENT DOCUMENTS

| | | | |
|---|---|---|---|
| 3,974,692 A | 8/1976 | Hassler |
| 4,055,988 A | 11/1977 | Dutton |
| 4,072,922 A | 2/1978 | Taner et al. |
| 4,097,835 A | 6/1978 | Green |
| 4,105,018 A | 8/1978 | Greenleaf et al. |
| 4,180,792 A | 12/1979 | Lederman et al. |
| 4,205,394 A | 5/1980 | Pickens |
| 4,229,798 A | 10/1980 | Rosie |
| 4,259,733 A | 3/1981 | Taner et al. |
| 4,265,126 A | 5/1981 | Papadofrangakis et al. |
| 4,271,842 A | 6/1981 | Specht et al. |
| 4,325,257 A | 4/1982 | Kino et al. |
| 4,327,738 A | 5/1982 | Green et al. |
| 4,328,569 A | 5/1982 | Trott et al. |
| 4,333,474 A | 6/1982 | Nigam |
| 4,339,952 A | 7/1982 | Foster |
| 4,452,084 A | 6/1984 | Taenzer |
| 4,501,279 A | 2/1985 | Seo |
| 4,511,998 A | 4/1985 | Kanda et al. |
| 4,539,847 A | 9/1985 | Paap |
| 4,566,459 A | 1/1986 | Umemura et al. |
| 4,567,768 A | 2/1986 | Satoh et al. |
| 4,604,697 A | 8/1986 | Luthra et al. |
| 4,662,222 A | 5/1987 | Johnson |
| 4,669,482 A | 6/1987 | Ophir |
| 4,682,497 A | 7/1987 | Sasaki |
| 4,694,434 A | 9/1987 | Von Ramm et al. |
| 4,781,199 A | 11/1988 | Hirama et al. |
| 4,817,434 A | 4/1989 | Anderson |
| 4,831,601 A | 5/1989 | Breimesser et al. |
| 4,893,284 A | 1/1990 | Magrane |
| 4,893,628 A | 1/1990 | Angelsen |
| 4,990,462 A | 2/1991 | Sliwa, Jr. |
| 5,027,658 A | 7/1991 | Anderson |
| 5,050,588 A | 9/1991 | Grey et al. |
| 5,060,205 A | 10/1991 | Phelan |
| 5,062,295 A | 11/1991 | Shakkottai et al. |
| 5,141,738 A | 8/1992 | Rasor et al. |
| 5,161,536 A | 11/1992 | Vilkomerson et al. |
| 5,197,475 A | 3/1993 | Antich et al. |
| 5,226,019 A | 7/1993 | Bahorich |
| 5,230,339 A | 7/1993 | Charlebois |
| 5,269,309 A | 12/1993 | Fort et al. |
| 5,278,757 A | 1/1994 | Hoctor et al. |
| 5,293,871 A | 3/1994 | Reinstein et al. |
| 5,299,576 A | 4/1994 | Shiba |
| 5,301,674 A | 4/1994 | Erikson et al. |
| 5,305,756 A | 4/1994 | Entrekin et al. |
| 5,339,282 A | 8/1994 | Kuhn et al. |
| 5,340,510 A | 8/1994 | Bowen |
| 5,345,426 A | 9/1994 | Lipschutz |
| 5,349,960 A | 9/1994 | Gondo |
| 5,355,888 A | 10/1994 | Kendall |
| 5,381,794 A | 1/1995 | Tel et al. |
| 5,398,216 A | 3/1995 | Hall et al. |
| 5,409,010 A | 4/1995 | Beach et al. |
| 5,442,462 A | 8/1995 | Guissin |
| 5,454,372 A | 10/1995 | Banjanin et al. |
| 5,477,858 A | 12/1995 | Norris et al. |
| 5,503,152 A | 4/1996 | Oakley et al. |
| 5,515,853 A | 5/1996 | Smith et al. |
| 5,515,856 A | 5/1996 | Olstad et al. |
| 5,522,393 A | 6/1996 | Phillips et al. |
| 5,526,815 A | 6/1996 | Granz et al. |
| 5,544,659 A | 8/1996 | Banjanin |
| 5,558,092 A | 9/1996 | Unger |
| 5,564,423 A | 10/1996 | Mele et al. |
| 5,568,812 A | 10/1996 | Murashita et al. |
| 5,570,691 A | 11/1996 | Wright et al. |
| 5,581,517 A | 12/1996 | Gee et al. |
| 5,625,149 A | 4/1997 | Gururaja et al. |
| 5,628,320 A | 5/1997 | Teo |
| 5,666,953 A | 9/1997 | Wilk |
| 5,673,697 A | 10/1997 | Bryan et al. |
| 5,675,550 A | 10/1997 | Ekhaus |
| 5,720,291 A | 2/1998 | Schwartz |
| 5,720,708 A | 2/1998 | Lu et al. |
| 5,744,898 A | 4/1998 | Smith et al. |
| 5,769,079 A | 6/1998 | Hossack |
| 5,784,334 A | 7/1998 | Sena et al. |
| 5,785,654 A | 7/1998 | Iinuma et al. |
| 5,795,297 A | 8/1998 | Daigle |
| 5,797,845 A | 8/1998 | Barabash et al. |
| 5,798,459 A | 8/1998 | Ohba et al. |
| 5,817,023 A | 10/1998 | Daft |
| 5,820,561 A | 10/1998 | Olstad et al. |
| 5,838,564 A | 11/1998 | Bahorich et al. |
| 5,850,622 A | 12/1998 | Vassiliou et al. |
| 5,862,100 A | 1/1999 | VerWest |
| 5,870,691 A | 2/1999 | Partyka et al. |
| 5,871,446 A | 2/1999 | Wilk |
| 5,876,342 A | 3/1999 | Chen et al. |
| 5,891,038 A | 4/1999 | Seyed-Bolorforosh et al. |
| 5,892,732 A | 4/1999 | Gersztenkorn |
| 5,916,169 A | 6/1999 | Hanafy et al. |
| 5,919,139 A | 7/1999 | Lin |
| 5,920,285 A | 7/1999 | Benjamin |
| 5,930,730 A | 7/1999 | Marfurt et al. |
| 5,938,612 A | 8/1999 | Kline-Schoder |
| 5,940,778 A | 8/1999 | Marfurt et al. |
| 5,951,479 A | 9/1999 | Holm et al. |
| 5,964,707 A | 10/1999 | Fenster et al. |

(56) References Cited

U.S. PATENT DOCUMENTS

| | | |
|---|---|---|
| 5,969,661 A | 10/1999 | Benjamin |
| 5,999,836 A | 12/1999 | Nelson et al. |
| 6,007,499 A | 12/1999 | Martin et al. |
| 6,013,032 A | 1/2000 | Savord |
| 6,014,473 A | 1/2000 | Hossack et al. |
| 6,048,315 A | 4/2000 | Chiao et al. |
| 6,049,509 A | 4/2000 | Sonneland et al. |
| 6,050,943 A | 4/2000 | Slayton et al. |
| 6,056,693 A | 5/2000 | Haider |
| 6,058,074 A | 5/2000 | Swan et al. |
| 6,077,224 A | 6/2000 | Lang et al. |
| 6,092,026 A | 7/2000 | Bahorich et al. |
| 6,122,538 A | 9/2000 | Sliwa, Jr. et al. |
| 6,123,670 A | 9/2000 | Mo |
| 6,129,672 A | 10/2000 | Seward et al. |
| 6,135,960 A | 10/2000 | Holmberg |
| 6,138,075 A | 10/2000 | Yost |
| 6,148,095 A | 11/2000 | Prause et al. |
| 6,162,175 A | 12/2000 | Marian, Jr. et al. |
| 6,166,384 A | 12/2000 | Dentinger et al. |
| 6,166,853 A | 12/2000 | Sapia et al. |
| 6,190,318 B1 | 2/2001 | Bab et al. |
| 6,193,665 B1 | 2/2001 | Hall et al. |
| 6,196,739 B1 | 3/2001 | Silverbrook |
| 6,200,266 B1 | 3/2001 | Shokrollahi et al. |
| 6,210,335 B1 | 4/2001 | Miller |
| 6,213,958 B1 | 4/2001 | Winder |
| 6,221,019 B1 | 4/2001 | Kantorovich |
| 6,224,556 B1 | 5/2001 | Schwartz et al. |
| 6,231,511 B1 | 5/2001 | Bae |
| 6,238,342 B1 | 5/2001 | Feleppa et al. |
| 6,246,901 B1 | 6/2001 | Benaron |
| 6,251,073 B1 | 6/2001 | Imran et al. |
| 6,264,609 B1 | 7/2001 | Herrington et al. |
| 6,266,551 B1 | 7/2001 | Osadchy et al. |
| 6,278,949 B1 | 8/2001 | Alam |
| 6,279,399 B1 | 8/2001 | Holm |
| 6,289,230 B1 | 9/2001 | Chaiken et al. |
| 6,299,580 B1 | 10/2001 | Asafusa |
| 6,304,684 B1 | 10/2001 | Niczyporuk et al. |
| 6,309,356 B1 | 10/2001 | Ustuner et al. |
| 6,324,453 B1 | 11/2001 | Breed et al. |
| 6,345,539 B1 | 2/2002 | Rawes et al. |
| 6,361,500 B1 | 3/2002 | Masters |
| 6,363,033 B1 | 3/2002 | Cole et al. |
| 6,370,480 B1 | 4/2002 | Gupta et al. |
| 6,373,984 B1 | 4/2002 | Gouge et al. |
| 6,374,185 B1 | 4/2002 | Taner et al. |
| 6,394,955 B1 | 5/2002 | Perlitz |
| 6,423,002 B1 | 7/2002 | Hossack |
| 6,431,175 B1 | 8/2002 | Penner et al. |
| 6,436,046 B1 | 8/2002 | Napolitano et al. |
| 6,449,821 B1 | 9/2002 | Sudol et al. |
| 6,450,965 B2 | 9/2002 | Williams et al. |
| 6,464,637 B1 | 10/2002 | Criton et al. |
| 6,468,216 B1 | 10/2002 | Powers et al. |
| 6,471,650 B2 | 10/2002 | Powers et al. |
| 6,475,150 B2 | 11/2002 | Haddad |
| 6,480,790 B1 | 11/2002 | Calvert et al. |
| 6,487,502 B1 | 11/2002 | Taner |
| 6,490,477 B1 | 12/2002 | Zylka et al. |
| 6,499,536 B1 | 12/2002 | Ellingsen |
| 6,503,204 B1 | 1/2003 | Sumanaweera et al. |
| 6,508,768 B1 | 1/2003 | Hall et al. |
| 6,508,770 B1 | 1/2003 | Cai |
| 6,514,205 B1 | 2/2003 | Lee et al. |
| 6,517,484 B1 | 2/2003 | Wilk et al. |
| 6,526,163 B1 | 2/2003 | Halmann et al. |
| 6,543,272 B1 | 4/2003 | Vitek |
| 6,547,732 B2 | 4/2003 | Jago |
| 6,551,246 B1 | 4/2003 | Ustuner et al. |
| 6,565,510 B1 | 5/2003 | Haider |
| 6,582,367 B1 | 6/2003 | Robinson et al. |
| 6,585,647 B1 | 7/2003 | Winder |
| 6,597,171 B2 | 7/2003 | Hurlimann et al. |
| 6,604,421 B1 | 8/2003 | Li |
| 6,614,560 B1 | 9/2003 | Silverbrook |
| 6,620,101 B2 | 9/2003 | Azzam et al. |
| 6,629,929 B1 | 10/2003 | Jago et al. |
| 6,645,147 B1 | 11/2003 | Jackosn et al. |
| 6,652,461 B1 | 11/2003 | Levkovitz |
| 6,668,654 B2 | 12/2003 | Dubois et al. |
| 6,672,165 B2 | 1/2004 | Rather et al. |
| 6,681,185 B1 | 1/2004 | Young et al. |
| 6,690,816 B2 | 2/2004 | Aylward et al. |
| 6,692,450 B1 | 2/2004 | Coleman |
| 6,695,778 B2 | 2/2004 | Golland et al. |
| 6,702,745 B1 | 3/2004 | Smythe |
| 6,704,692 B1 | 3/2004 | Banerjee et al. |
| 6,719,693 B2 | 4/2004 | Richard |
| 6,728,567 B2 | 4/2004 | Rather et al. |
| 6,752,762 B1 | 6/2004 | DeJong et al. |
| 6,755,787 B2 | 6/2004 | Hossack et al. |
| 6,780,152 B2 | 8/2004 | Ustuner et al. |
| 6,790,182 B2 | 9/2004 | Eck et al. |
| 6,835,178 B1 | 12/2004 | Wilson et al. |
| 6,837,853 B2 | 1/2005 | Marian |
| 6,843,770 B2 | 1/2005 | Sumanaweera |
| 6,847,737 B1 | 1/2005 | Kouri et al. |
| 6,854,332 B2 | 2/2005 | Alleyne |
| 6,865,140 B2 | 3/2005 | Thomenius et al. |
| 6,932,767 B2 | 8/2005 | Landry et al. |
| 7,033,320 B2 | 4/2006 | Von Behren et al. |
| 7,087,023 B2 | 8/2006 | Daft et al. |
| 7,104,956 B1 | 9/2006 | Christopher |
| 7,217,243 B2 | 5/2007 | Takeuchi |
| 7,221,867 B2 | 5/2007 | Silverbrook |
| 7,231,072 B2 | 6/2007 | Yamano et al. |
| 7,269,299 B2 | 9/2007 | Schroeder |
| 7,283,652 B2 | 10/2007 | Mendonca et al. |
| 7,285,094 B2 | 10/2007 | Nohara et al. |
| 7,293,462 B2 | 11/2007 | Lee et al. |
| 7,313,053 B2 | 12/2007 | Wodnicki |
| 7,366,704 B2 | 4/2008 | Reading et al. |
| 7,402,136 B2 | 7/2008 | Hossack et al. |
| 7,410,469 B1 | 8/2008 | Talish et al. |
| 7,415,880 B2 | 8/2008 | Renzel |
| 7,443,765 B2 | 10/2008 | Thomenius et al. |
| 7,444,875 B1 | 11/2008 | Wu et al. |
| 7,447,535 B2 | 11/2008 | Lavi |
| 7,448,998 B2 | 11/2008 | Robinson |
| 7,466,848 B2 | 12/2008 | Metaxas et al. |
| 7,469,096 B2 | 12/2008 | Silverbrook |
| 7,474,778 B2 | 1/2009 | Shinomura et al. |
| 7,481,577 B2 | 1/2009 | Ramamurthy et al. |
| 7,491,171 B2 | 2/2009 | Barthe et al. |
| 7,497,828 B1 | 3/2009 | Wilk et al. |
| 7,497,830 B2 | 3/2009 | Li |
| 7,510,529 B2 | 3/2009 | Chou et al. |
| 7,514,851 B2 | 4/2009 | Wilser et al. |
| 7,549,962 B2 | 6/2009 | Dreschel et al. |
| 7,574,026 B2 | 8/2009 | Rasche et al. |
| 7,625,343 B2 | 12/2009 | Cao et al. |
| 7,637,869 B2 | 12/2009 | Sudol |
| 7,668,583 B2 | 2/2010 | Fegert et al. |
| 7,674,228 B2 | 3/2010 | Williams et al. |
| 7,682,311 B2 | 3/2010 | Simopoulos et al. |
| 7,699,776 B2 | 4/2010 | Walker et al. |
| 7,722,541 B2 | 5/2010 | Cai |
| 7,744,532 B2 | 6/2010 | Ustuner et al. |
| 7,750,311 B2 | 7/2010 | Daghighian |
| 7,764,984 B2 | 7/2010 | Desmedt et al. |
| 7,785,260 B2 | 8/2010 | Umemura et al. |
| 7,787,680 B2 | 8/2010 | Ahn et al. |
| 7,806,828 B2 | 10/2010 | Stringer |
| 7,819,810 B2 | 10/2010 | Stringer et al. |
| 7,822,250 B2 | 10/2010 | Yao et al. |
| 7,824,337 B2 | 11/2010 | Abe et al. |
| 7,833,163 B2 | 11/2010 | Cai |
| 7,837,624 B1 | 11/2010 | Hossack et al. |
| 7,846,097 B2 | 12/2010 | Jones et al. |
| 7,850,613 B2 | 12/2010 | Stribling |
| 7,862,508 B2 | 1/2011 | Davies et al. |
| 7,876,945 B2 | 1/2011 | Lötjönen |

(56) References Cited

U.S. PATENT DOCUMENTS

| | | |
|---|---|---|
| 7,880,154 B2 | 2/2011 | Otto |
| 7,887,486 B2 | 2/2011 | Ustuner et al. |
| 7,901,358 B2 | 3/2011 | Mehl et al. |
| 7,914,451 B2 | 3/2011 | Davies |
| 7,919,906 B2 | 4/2011 | Cerofolini |
| 7,926,350 B2 | 4/2011 | Kröning et al. |
| 7,927,280 B2 | 4/2011 | Davidsen |
| 7,972,271 B2 | 7/2011 | Johnson et al. |
| 7,984,637 B2 | 7/2011 | Ao et al. |
| 7,984,651 B2 | 7/2011 | Randall et al. |
| 8,002,705 B1 | 8/2011 | Napolitano et al. |
| 8,007,439 B2 | 8/2011 | Specht |
| 8,057,392 B2 | 11/2011 | Hossack et al. |
| 8,057,393 B2 | 11/2011 | Yao et al. |
| 8,079,263 B2 | 12/2011 | Randall et al. |
| 8,079,956 B2 | 12/2011 | Azuma et al. |
| 8,088,067 B2 | 1/2012 | Vortman et al. |
| 8,088,068 B2 | 1/2012 | Yao et al. |
| 8,088,071 B2 | 1/2012 | Hwang et al. |
| 8,105,239 B2 | 1/2012 | Specht |
| 8,135,190 B2 | 3/2012 | Bae et al. |
| 8,157,737 B2 | 4/2012 | Zhang et al. |
| 8,182,427 B2 | 5/2012 | Wu et al. |
| 8,202,219 B2 | 6/2012 | Luo et al. |
| 8,265,175 B2 | 9/2012 | Barsoum et al. |
| 8,277,383 B2 | 10/2012 | Specht |
| 8,279,705 B2 | 10/2012 | Choi et al. |
| 8,412,307 B2 | 4/2013 | Willis et al. |
| 8,414,564 B2 | 4/2013 | Goldshleger et al. |
| 8,419,642 B2 | 4/2013 | Sandrin et al. |
| 8,473,239 B2 | 6/2013 | Specht et al. |
| 8,478,382 B2 | 7/2013 | Burnside et al. |
| 8,483,804 B2 | 7/2013 | Hsieh et al. |
| 8,532,951 B2 | 9/2013 | Roy et al. |
| 8,539,838 B2 | 9/2013 | Yoo et al. |
| 8,582,848 B2 | 11/2013 | Funka-Lea et al. |
| 8,602,993 B2 | 12/2013 | Specht et al. |
| 8,627,724 B2 | 1/2014 | Papadopoulos et al. |
| 8,634,615 B2 | 1/2014 | Brabec |
| 8,672,846 B2 | 3/2014 | Napolitano et al. |
| 8,684,936 B2 | 4/2014 | Specht |
| 9,036,887 B2 | 5/2015 | Fouras et al. |
| 9,072,495 B2 | 7/2015 | Specht |
| 9,146,313 B2 | 9/2015 | Specht et al. |
| 9,192,355 B2 | 11/2015 | Smith et al. |
| 9,220,478 B2 | 12/2015 | Smith et al. |
| 9,247,926 B2 | 2/2016 | Smith et al. |
| 9,265,484 B2 | 2/2016 | Brewer et al. |
| 9,282,945 B2 | 3/2016 | Smith et al. |
| 9,339,256 B2 | 5/2016 | Specht et al. |
| 9,392,986 B2 | 7/2016 | Ning et al. |
| 9,420,994 B2 | 8/2016 | Specht |
| 9,510,806 B2 | 12/2016 | Smith et al. |
| 9,526,475 B2 | 12/2016 | Specht et al. |
| 9,572,549 B2 | 2/2017 | Belevich et al. |
| 9,582,876 B2 | 2/2017 | Specht |
| 9,606,206 B2 | 3/2017 | Boernert et al. |
| 9,668,714 B2 | 6/2017 | Call et al. |
| 9,788,813 B2 | 10/2017 | Adam et al. |
| 9,883,848 B2 | 2/2018 | Specht et al. |
| 9,986,969 B2 | 6/2018 | Call et al. |
| 9,986,975 B2 | 6/2018 | Specht et al. |
| 10,064,605 B2 | 9/2018 | Belevich et al. |
| 10,130,333 B2 | 11/2018 | Specht |
| 10,206,662 B2 | 2/2019 | Smith et al. |
| 10,226,234 B2 | 3/2019 | Specht et al. |
| 10,267,913 B2 | 4/2019 | Smith et al. |
| 10,342,518 B2 | 7/2019 | Specht et al. |
| 10,380,399 B2 | 8/2019 | Call et al. |
| 10,401,493 B2 | 9/2019 | Call et al. |
| 10,617,384 B2 | 4/2020 | Brewer et al. |
| 10,653,392 B2 | 5/2020 | Specht et al. |
| 10,675,000 B2 | 6/2020 | Specht et al. |
| 10,695,027 B2 | 6/2020 | Call et al. |
| 10,835,208 B2 | 11/2020 | Smith et al. |
| 10,856,846 B2 | 12/2020 | Davis et al. |
| 10,925,577 B2 | 2/2021 | Adam et al. |
| 11,016,191 B2 | 5/2021 | Call et al. |
| 11,051,791 B2 | 7/2021 | Smith et al. |
| 11,068,689 B2 | 7/2021 | Call et al. |
| 11,096,662 B2 | 8/2021 | Specht |
| 11,172,911 B2 | 11/2021 | Call et al. |
| 11,253,233 B2 | 2/2022 | Belevich et al. |
| 11,464,492 B2 | 10/2022 | Specht et al. |
| 2002/0035864 A1 | 3/2002 | Paltieli et al. |
| 2002/0073781 A1 | 6/2002 | Hashimoto et al. |
| 2002/0087071 A1 | 7/2002 | Schmitz et al. |
| 2002/0111568 A1 | 8/2002 | Bukshpan |
| 2002/0138003 A1 | 9/2002 | Bukshpan |
| 2002/0161299 A1 | 10/2002 | Prater et al. |
| 2003/0007598 A1 | 1/2003 | Wang et al. |
| 2003/0013962 A1 | 1/2003 | Bjaerum et al. |
| 2003/0028111 A1 | 2/2003 | Vaezy et al. |
| 2003/0040669 A1 | 2/2003 | Grass et al. |
| 2003/0163271 A1 | 9/2003 | Chell et al. |
| 2003/0181806 A1 | 9/2003 | Medan et al. |
| 2003/0220554 A1 | 11/2003 | Grenon et al. |
| 2003/0228053 A1 | 12/2003 | Li et al. |
| 2004/0015079 A1 | 1/2004 | Berger et al. |
| 2004/0054283 A1 | 3/2004 | Corey et al. |
| 2004/0068184 A1 | 4/2004 | Trahey et al. |
| 2004/0100163 A1 | 5/2004 | Baumgartner et al. |
| 2004/0111028 A1 | 6/2004 | Abe et al. |
| 2004/0122313 A1 | 6/2004 | Moore et al. |
| 2004/0122322 A1 | 6/2004 | Moore et al. |
| 2004/0127793 A1 | 7/2004 | Mendlein et al. |
| 2004/0138565 A1 | 7/2004 | Trucco |
| 2004/0144176 A1 | 7/2004 | Yoden |
| 2004/0215075 A1 | 10/2004 | Zagzebski et al. |
| 2004/0236217 A1 | 11/2004 | Cerwin et al. |
| 2004/0236223 A1 | 11/2004 | Barnes et al. |
| 2004/0258127 A1 | 12/2004 | Ramamurthy et al. |
| 2004/0267132 A1 | 12/2004 | Podany |
| 2005/0004449 A1 | 1/2005 | Mitschke et al. |
| 2005/0053305 A1 | 3/2005 | Li et al. |
| 2005/0054910 A1 | 3/2005 | Tremblay et al. |
| 2005/0061536 A1 | 3/2005 | Proulx |
| 2005/0090743 A1 | 4/2005 | Kawashima et al. |
| 2005/0090745 A1 | 4/2005 | Steen |
| 2005/0111846 A1 | 5/2005 | Steinbacher et al. |
| 2005/0113689 A1 | 5/2005 | Gritzky |
| 2005/0113694 A1 | 5/2005 | Haugen et al. |
| 2005/0124883 A1 | 6/2005 | Hunt |
| 2005/0131300 A1 | 6/2005 | Bakircioglu et al. |
| 2005/0147297 A1 | 7/2005 | McLaughlin et al. |
| 2005/0165312 A1 | 7/2005 | Knowles et al. |
| 2005/0203404 A1 | 9/2005 | Freiburger |
| 2005/0215883 A1 | 9/2005 | Hundley et al. |
| 2005/0240125 A1 | 10/2005 | Makin et al. |
| 2005/0252295 A1 | 11/2005 | Fink et al. |
| 2005/0281447 A1 | 12/2005 | Moreau-Gobard et al. |
| 2005/0288588 A1 | 12/2005 | Weber et al. |
| 2006/0036170 A1 | 2/2006 | Lachaine et al. |
| 2006/0058664 A1 | 3/2006 | Barthe et al. |
| 2006/0062447 A1 | 3/2006 | Rinck et al. |
| 2006/0074313 A1 | 4/2006 | Slayton et al. |
| 2006/0074315 A1 | 4/2006 | Liang et al. |
| 2006/0074320 A1 | 4/2006 | Yoo et al. |
| 2006/0079759 A1 | 4/2006 | Vaillant et al. |
| 2006/0079778 A1 | 4/2006 | Mo et al. |
| 2006/0079782 A1 | 4/2006 | Beach et al. |
| 2006/0094962 A1 | 5/2006 | Clark |
| 2006/0111634 A1 | 5/2006 | Wu |
| 2006/0122506 A1 | 6/2006 | Davies et al. |
| 2006/0173327 A1 | 8/2006 | Kim |
| 2006/0256231 A1 | 11/2006 | Sasaki et al. |
| 2006/0262961 A1 | 11/2006 | Holsing et al. |
| 2006/0270934 A1 | 11/2006 | Savord et al. |
| 2007/0016022 A1 | 1/2007 | Blalock et al. |
| 2007/0016044 A1 | 1/2007 | Blalock et al. |
| 2007/0036414 A1 | 2/2007 | Georgescu et al. |
| 2007/0043290 A1 | 2/2007 | Goepp et al. |
| 2007/0055155 A1 | 3/2007 | Owen et al. |
| 2007/0073781 A1 | 3/2007 | Adkins et al. |

(56) References Cited

U.S. PATENT DOCUMENTS

| | | |
|---|---|---|
| 2007/0078345 A1 | 4/2007 | Mo et al. |
| 2007/0083109 A1 | 4/2007 | Ustuner et al. |
| 2007/0088213 A1 | 4/2007 | Poland |
| 2007/0138157 A1 | 6/2007 | Dane et al. |
| 2007/0161898 A1 | 7/2007 | Hao et al. |
| 2007/0161904 A1 | 7/2007 | Urbano |
| 2007/0167752 A1 | 7/2007 | Proulx et al. |
| 2007/0167824 A1 | 7/2007 | Lee et al. |
| 2007/0232914 A1 | 10/2007 | Chen et al. |
| 2007/0238985 A1 | 10/2007 | Smith et al. |
| 2007/0242567 A1 | 10/2007 | Daft et al. |
| 2008/0044572 A1 | 2/2008 | Loeffler et al. |
| 2008/0110261 A1 | 5/2008 | Randall et al. |
| 2008/0110263 A1 | 5/2008 | Klessel et al. |
| 2008/0112265 A1 | 5/2008 | Urbano et al. |
| 2008/0114241 A1 | 5/2008 | Randall et al. |
| 2008/0114245 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114255 A1 | 5/2008 | Schwartz et al. |
| 2008/0125659 A1 | 5/2008 | Wilser et al. |
| 2008/0132790 A1 | 6/2008 | Burton |
| 2008/0181479 A1 | 7/2008 | Yang et al. |
| 2008/0183075 A1 | 7/2008 | Govari et al. |
| 2008/0188747 A1 | 8/2008 | Randall et al. |
| 2008/0188750 A1 | 8/2008 | Randall et al. |
| 2008/0194957 A1 | 8/2008 | Hoctor et al. |
| 2008/0194958 A1 | 8/2008 | Lee et al. |
| 2008/0194959 A1 | 8/2008 | Wang et al. |
| 2008/0208061 A1 | 8/2008 | Halmann |
| 2008/0242996 A1 | 10/2008 | Hall et al. |
| 2008/0249408 A1 | 10/2008 | Palmeri et al. |
| 2008/0255452 A1 | 10/2008 | Entrekin |
| 2008/0262357 A1 | 10/2008 | Wodnicki |
| 2008/0269604 A1 | 10/2008 | Boctor et al. |
| 2008/0269613 A1 | 10/2008 | Summers et al. |
| 2008/0275344 A1 | 11/2008 | Glide-Hurst et al. |
| 2008/0285819 A1 | 11/2008 | Konofagou et al. |
| 2008/0287787 A1 | 11/2008 | Sauer et al. |
| 2008/0294045 A1 | 11/2008 | Ellington et al. |
| 2008/0294050 A1 | 11/2008 | Shinomura et al. |
| 2008/0294052 A1 | 11/2008 | Wilser et al. |
| 2008/0306382 A1 | 12/2008 | Guracar et al. |
| 2008/0306386 A1 | 12/2008 | Baba et al. |
| 2008/0319317 A1 | 12/2008 | Kamiyama et al. |
| 2008/0319318 A1 | 12/2008 | Johnson et al. |
| 2009/0005679 A1 | 1/2009 | Dala-Krishna |
| 2009/0010459 A1 | 1/2009 | Garbini et al. |
| 2009/0012393 A1 | 1/2009 | Choi |
| 2009/0015665 A1 | 1/2009 | Willsie |
| 2009/0016163 A1 | 1/2009 | Freeman et al. |
| 2009/0018445 A1 | 1/2009 | Schers et al. |
| 2009/0024039 A1 | 1/2009 | Wang et al. |
| 2009/0036780 A1 | 2/2009 | Abraham |
| 2009/0043206 A1 | 2/2009 | Towfiq et al. |
| 2009/0048519 A1 | 2/2009 | Hossack et al. |
| 2009/0069681 A1 | 3/2009 | Lundberg et al. |
| 2009/0069686 A1 | 3/2009 | Daft et al. |
| 2009/0069692 A1 | 3/2009 | Cooley et al. |
| 2009/0079299 A1 | 3/2009 | Bradley et al. |
| 2009/0099483 A1 | 4/2009 | Rybyanets |
| 2009/0112095 A1 | 4/2009 | Daigle |
| 2009/0131797 A1 | 5/2009 | Jeong et al. |
| 2009/0143680 A1 | 6/2009 | Yao et al. |
| 2009/0148012 A1 | 6/2009 | Altmann et al. |
| 2009/0150094 A1 | 6/2009 | Van Velsor et al. |
| 2009/0182233 A1 | 7/2009 | Wodnicki |
| 2009/0182237 A1 | 7/2009 | Angelsen et al. |
| 2009/0198134 A1 | 8/2009 | Hashimoto et al. |
| 2009/0203997 A1 | 8/2009 | Ustuner |
| 2009/0208080 A1 | 8/2009 | Grau et al. |
| 2009/0259128 A1 | 10/2009 | Stribling |
| 2009/0264760 A1 | 10/2009 | Lazebnik et al. |
| 2009/0306510 A1 | 12/2009 | Hashiba et al. |
| 2009/0326379 A1 | 12/2009 | Daigle et al. |
| 2010/0010354 A1 | 1/2010 | Skert et al. |
| 2010/0016725 A1 | 1/2010 | Thiele |
| 2010/0036258 A1 | 2/2010 | Dietz et al. |
| 2010/0063397 A1 | 3/2010 | Wagner |
| 2010/0063399 A1 | 3/2010 | Walker et al. |
| 2010/0069751 A1 | 3/2010 | Hazard et al. |
| 2010/0069756 A1 | 3/2010 | Ogasawara et al. |
| 2010/0085383 A1 | 4/2010 | Cohen et al. |
| 2010/0106431 A1 | 4/2010 | Baba et al. |
| 2010/0109481 A1 | 5/2010 | Buccafusca |
| 2010/0121193 A1 | 5/2010 | Fukukita et al. |
| 2010/0121196 A1 | 5/2010 | Hwang et al. |
| 2010/0130855 A1 | 5/2010 | Lundberg et al. |
| 2010/0145195 A1 | 6/2010 | Hyun |
| 2010/0168566 A1 | 7/2010 | Bercoff et al. |
| 2010/0168578 A1 | 7/2010 | Garson, Jr. et al. |
| 2010/0174194 A1 | 7/2010 | Chiang et al. |
| 2010/0174198 A1 | 7/2010 | Young et al. |
| 2010/0191110 A1 | 7/2010 | Insana et al. |
| 2010/0217124 A1 | 8/2010 | Cooley |
| 2010/0217125 A1 | 8/2010 | Kadokura et al. |
| 2010/0228126 A1 | 9/2010 | Emery et al. |
| 2010/0240994 A1 | 9/2010 | Zheng |
| 2010/0249570 A1 | 9/2010 | Carson et al. |
| 2010/0249596 A1 | 9/2010 | Magee |
| 2010/0256488 A1 | 10/2010 | Kim et al. |
| 2010/0262013 A1 | 10/2010 | Smith et al. |
| 2010/0266176 A1 | 10/2010 | Masumoto et al. |
| 2010/0286525 A1 | 11/2010 | Osumi |
| 2010/0286527 A1 | 11/2010 | Cannon et al. |
| 2010/0298712 A1 | 11/2010 | Pelissier et al. |
| 2010/0310143 A1 | 12/2010 | Rao et al. |
| 2010/0317971 A1 | 12/2010 | Fan et al. |
| 2010/0324418 A1 | 12/2010 | El-Aklouk et al. |
| 2010/0324423 A1 | 12/2010 | El-Aklouk et al. |
| 2010/0329521 A1 | 12/2010 | Beymer et al. |
| 2011/0005322 A1 | 1/2011 | Ustuner |
| 2011/0016977 A1 | 1/2011 | Guracar |
| 2011/0021920 A1 | 1/2011 | Shafir et al. |
| 2011/0021923 A1 | 1/2011 | Daft et al. |
| 2011/0033098 A1 | 2/2011 | Richter et al. |
| 2011/0044133 A1 | 2/2011 | Tokita |
| 2011/0066030 A1 | 3/2011 | Yao |
| 2011/0098565 A1 | 4/2011 | Masuzawa |
| 2011/0112400 A1 | 5/2011 | Emery et al. |
| 2011/0112404 A1 | 5/2011 | Gourevitch |
| 2011/0125017 A1 | 5/2011 | Ramamurthy et al. |
| 2011/0178441 A1 | 7/2011 | Tyler |
| 2011/0213244 A1 | 9/2011 | Frinking et al. |
| 2011/0270088 A1 | 11/2011 | Shiina |
| 2011/0301470 A1 | 12/2011 | Sato et al. |
| 2011/0306886 A1 | 12/2011 | Daft et al. |
| 2011/0319764 A1 | 12/2011 | Okada et al. |
| 2012/0004545 A1 | 1/2012 | Ziv-Ari et al. |
| 2012/0035482 A1 | 2/2012 | Kim et al. |
| 2012/0036934 A1 | 2/2012 | Kröning et al. |
| 2012/0085173 A1 | 4/2012 | Papadopoulos et al. |
| 2012/0101378 A1 | 4/2012 | Lee |
| 2012/0114210 A1 | 5/2012 | Kim et al. |
| 2012/0121150 A1 | 5/2012 | Murashita |
| 2012/0137778 A1 | 6/2012 | Kitazawa et al. |
| 2012/0140595 A1 | 6/2012 | Amemiya |
| 2012/0141002 A1 | 6/2012 | Urbano et al. |
| 2012/0165670 A1 | 6/2012 | Shi et al. |
| 2012/0179044 A1 | 7/2012 | Chiang et al. |
| 2012/0209150 A1 | 8/2012 | Zeng et al. |
| 2012/0226201 A1 | 9/2012 | Clark et al. |
| 2012/0243763 A1 | 9/2012 | Wen et al. |
| 2013/0030296 A1 | 1/2013 | Miyaki |
| 2013/0070062 A1 | 3/2013 | Fouras et al. |
| 2013/0131516 A1 | 5/2013 | Katsuyama |
| 2013/0144165 A1 | 6/2013 | Ebbini et al. |
| 2013/0258805 A1 | 10/2013 | Hansen et al. |

(56) References Cited

U.S. PATENT DOCUMENTS

| | | | |
|---|---|---|---|
| 2013/0261463 | A1 | 10/2013 | Chiang et al. |
| 2014/0073921 | A1 | 3/2014 | Specht et al. |
| 2014/0147013 | A1 | 5/2014 | Shandas et al. |
| 2015/0045668 | A1 | 2/2015 | Smith et al. |
| 2018/0153511 | A1 | 6/2018 | Specht et al. |
| 2019/0200961 | A1 | 7/2019 | Specht et al. |
| 2020/0275910 | A1 | 9/2020 | Specht et al. |
| 2020/0297320 | A1 | 9/2020 | Specht et al. |
| 2020/0323513 | A1 | 10/2020 | Call et al. |
| 2021/0068787 | A1 | 3/2021 | Smith et al. |
| 2021/0085292 | A1 | 3/2021 | Davis et al. |
| 2021/0278531 | A1 | 9/2021 | Call et al. |
| 2021/0350101 | A1 | 11/2021 | Call et al. |
| 2021/0378633 | A1 | 12/2021 | Specht et al. |
| 2022/0071601 | A1 | 3/2022 | Call et al. |
| 2022/0167949 | A1 | 6/2022 | Belevich et al. |
| 2023/0277158 | A1 | 9/2023 | Brewer et al. |
| 2023/0380805 | A1 | 11/2023 | Specht et al. |

FOREIGN PATENT DOCUMENTS

| | | | |
|---|---|---|---|
| CN | 1781460 | A | 6/2006 |
| CN | 101103927 | A | 1/2008 |
| CN | 101116622 | A | 2/2008 |
| CN | 101190134 | A | 6/2008 |
| CN | 101453955 | A | 6/2009 |
| CN | 100545650 | C | 9/2009 |
| CN | 101609150 | A | 12/2009 |
| CN | 101852773 | A | 6/2010 |
| CN | 101785684 | A | 7/2010 |
| CN | 101843501 | A | 9/2010 |
| CN | 101912278 | A | 12/2010 |
| CN | 102018533 | A | 4/2011 |
| CN | 102112047 | A | 6/2011 |
| CN | 102123668 | A | 7/2011 |
| EP | 1346689 | A2 | 9/2003 |
| EP | 1949856 | A1 | 7/2008 |
| EP | 2058796 | A2 | 5/2009 |
| EP | 2101191 | A2 | 9/2009 |
| EP | 2182352 | A2 | 5/2010 |
| EP | 2187813 | A1 | 5/2010 |
| EP | 2198785 | A1 | 6/2010 |
| EP | 1757955 | B1 | 11/2010 |
| EP | 2319417 | A1 | 5/2011 |
| EP | 2325672 | A1 | 5/2011 |
| EP | 1462819 | B1 | 7/2011 |
| EP | 2356941 | A1 | 8/2011 |
| EP | 1979739 | B1 | 10/2011 |
| EP | 2385391 | A2 | 11/2011 |
| EP | 2294400 | B1 | 2/2012 |
| EP | 2453256 | A2 | 5/2012 |
| EP | 1840594 | B1 | 6/2012 |
| EP | 1850743 | B1 | 12/2012 |
| EP | 1594404 | B1 | 9/2013 |
| EP | 2026280 | B1 | 10/2013 |
| FR | 2851662 | A1 | 8/2004 |
| JP | 49-11189 | A | 1/1974 |
| JP | 54-44375 | A | 4/1979 |
| JP | 55-103839 | A | 8/1980 |
| JP | 57-31848 | A | 2/1982 |
| JP | 58-223059 | A | 12/1983 |
| JP | 59-101143 | A | 6/1984 |
| JP | 59-174151 | A | 10/1984 |
| JP | 60-13109 | U | 1/1985 |
| JP | 60-68836 | A | 4/1985 |
| JP | 01164354 | A | 6/1989 |
| JP | 02501431 | A | 5/1990 |
| JP | 03015455 | A | 1/1991 |
| JP | 03126443 | A | 5/1991 |
| JP | 04017842 | A | 1/1992 |
| JP | 04067856 | A | 3/1992 |
| JP | 05042138 | A | 2/1993 |
| JP | H05146437 | A | 6/1993 |
| JP | 06125908 | A | 5/1994 |
| JP | 06254092 | A | 9/1994 |
| JP | 07051266 | A | 2/1995 |
| JP | 07204201 | A | 8/1995 |
| JP | H07204202 | A | 8/1995 |
| JP | 08154930 | A | 6/1996 |
| JP | 08252253 | A | 10/1996 |
| JP | H0315455 | A | 1/1997 |
| JP | 09103429 | A | 4/1997 |
| JP | 09201361 | A | 8/1997 |
| JP | 2777197 | B | 5/1998 |
| JP | 10216128 | A | 8/1998 |
| JP | 11089833 | A | 4/1999 |
| JP | 11239578 | A | 9/1999 |
| JP | 2001507794 | A | 6/2001 |
| JP | 2001245884 | A | 9/2001 |
| JP | 2002209894 | A | 7/2002 |
| JP | 2002253548 | A | 9/2002 |
| JP | 2002253549 | A | 9/2002 |
| JP | 2003235839 | A | 8/2003 |
| JP | 2003290224 | A | 10/2003 |
| JP | 2004167092 | A | 6/2004 |
| JP | 2004215987 | A | 8/2004 |
| JP | 2004337457 | A | 12/2004 |
| JP | 2004340809 | A | 12/2004 |
| JP | 2004351214 | A | 12/2004 |
| JP | 2005046192 | A | 2/2005 |
| JP | 2005046193 | A | 2/2005 |
| JP | 2005152187 | A | 6/2005 |
| JP | 2005523792 | A | 8/2005 |
| JP | 2005526539 | A | 9/2005 |
| JP | 2006051356 | A | 2/2006 |
| JP | 2006061203 | A | 3/2006 |
| JP | 2006122657 | A | 5/2006 |
| JP | 2006130313 | A | 5/2006 |
| JP | 2006204923 | A | 8/2006 |
| JP | 2007325937 | A | 12/2007 |
| JP | 2008122209 | A | 5/2008 |
| JP | 2008513763 | A | 5/2008 |
| JP | 2008515557 | A | 5/2008 |
| JP | 2008132342 | A | 6/2008 |
| JP | 2008522642 | A | 7/2008 |
| JP | 2008259541 | A | 10/2008 |
| JP | 2008279274 | A | 11/2008 |
| JP | 2008307087 | A | 12/2008 |
| JP | 2009178448 | A | 8/2009 |
| JP | 2009240667 | A | 10/2009 |
| JP | 2010005375 | A | 1/2010 |
| JP | 2010124842 | A | 6/2010 |
| JP | 2010526626 | A | 8/2010 |
| JP | 2010227503 | A | 10/2010 |
| JP | 2011529362 | A | 12/2011 |
| KR | 100715132 | B | 4/2007 |
| KR | 1020080044737 | A | 5/2008 |
| KR | 1020090009258 | A | 1/2009 |
| KR | 1020090103408 | A | 10/2009 |
| KR | 1020100051108 | A | 5/2010 |
| WO | WO92/18054 | A1 | 10/1992 |
| WO | WO98/00719 | A2 | 1/1998 |
| WO | WO01/64109 | A1 | 9/2001 |
| WO | WO02/084594 | A2 | 10/2002 |
| WO | WO2005/009245 | A1 | 2/2005 |
| WO | WO2006/113445 | A1 | 10/2006 |
| WO | WO2006/114735 | A1 | 11/2006 |
| WO | WO2007/127147 | A2 | 11/2007 |
| WO | WO2008/097479 | A1 | 8/2008 |
| WO | WO2008/137030 | A1 | 11/2008 |
| WO | WO2009/060182 | A2 | 5/2009 |
| WO | WO2010/095094 | A1 | 8/2010 |
| WO | WO2010/137453 | A1 | 12/2010 |
| WO | WO2010/139519 | A1 | 12/2010 |
| WO | WO2011/004661 | A1 | 1/2011 |
| WO | WO2011/057252 | A1 | 5/2011 |
| WO | WO2011/064688 | A1 | 6/2011 |
| WO | WO2011/094585 | A | 8/2011 |
| WO | WO2011/100697 | A1 | 8/2011 |
| WO | WO2011/123529 | A1 | 10/2011 |
| WO | WO2012/028896 | A1 | 3/2012 |
| WO | WO2012/049124 | A2 | 4/2012 |
| WO | WO2012/049612 | A2 | 4/2012 |

(56) References Cited

FOREIGN PATENT DOCUMENTS

| WO | WO2012/078639 A1 | 6/2012 |
|----|------------------|--------|
| WO | WO2012/091280 A1 | 7/2012 |
| WO | WO2012/112540 A2 | 8/2012 |

OTHER PUBLICATIONS

Arigovindan et al.; Full motion and flow field recovery from echo doppler data; IEEE Transactions on Medical Imaging; 26(1); pp. 31-45; Jan. 2007.
Cai et al.; Off-axis directional acoustic wave beaming control by an asymmetric rubber heterostructures film deposited on steel plate in water; IEEE Intl.; 2009 Ultrasonics Symposium (IUS); pp. 1552-1554; Rome; Sep. 2009.
Capineri et al.; A doppler system for dynamic vector velocity maps; Ultrasound in Medicine & Biology; 28(2); pp. 237-248; Feb. 28, 2002.
Carson et al.; Measurement of photoacoustic transducer position by robotic source placement and nonlinear parameter estimation; Biomedical Optics (BIOS); International Society for Optics and Photonics (9th Conf. on Biomedical Thermoacoustics, Optoacoustics, and Acousto-optics; vol. 6656; 9 pages; Feb. 28, 2008.
Chen et al.; Maximum-likelihood source localization and unknown sensor location estimation for wideband signals in the near-field; IEEE Transactions On Signal Processing; 50(8); pp. 1843-1854; Aug. 2002.
Chen et al.; Source localization and tracking of a wideband source using a randomly distributed beamforming sensor array; International Journal of High Performance Computing Applications: 16(3); pp. 259-272; Fall 2002.
Cristianini et al.; An Introduction to Support Vector Machines; Cambridge University Press; pp. 93-111; Mar. 2000.
Dunmire et al.; A brief history of vector doppler; Medical Imaging 2001; International Society for Optics and Photonics; pp. 200-214; May 30, 2001.
Dunmire et al.; Cross-beam vector Doppler ultrasound for angle-independent velocity measurements; Ultrasound in medicine & biology; 26(8); pp. 1213-1235; Oct. 2000.
Du et al.; User parameter free approaches to multistatic adaptive ultrasound imaging; 5th IEEE International Symposium; pp. 1287-1290, May 2008.
Feigenbaum, Harvey, M.D.; Echocardiography; Lippincott Williams & Wilkins; Philadelphia; 5th Ed.; pp. 482, 484; Feb. 1994.
Fernandez et al.; High resolution ultrasound beamforming using synthetic and adaptive imaging techniques; Proceedings IEEE International Symposium on Biomedical Imaging; Washington, D.C.; pp. 433-436; Jul. 7-10, 2002.
Gazor et al.; Wideband multi-source beamforming with array location calibration and direction finding; Conference on Acoustics, Speech and Signal Processing ICASSP-95; Detroit, MI; vol. 3 IEEE; pp. 1904-1907; May 9-12, 1995.
Gran et al.; Directional velocity estimation using a spatio-temporal encoding technique based on frequency division for synthetic transmit aperture ultrasound; IEEE transactions on ultrasonics, ferroelectrics, and frequency control; 53 (7); pp. 1289-1299, Aug. 2006.
Haun et al.; Efficient three-dimensional imaging from a small cylindrical aperture; IEEE Trans. on Ultrasonics, Ferroelectrics, and Frequency Control; 49(7); pp. 861-870; Jul. 2002.
Haykin, Simon; Neural Networks: A Comprehensive Foundation (2nd Ed.); Prentice Hall; pp. 156-187; Jul. 16, 1998.
Heikkila et al.; A four-step camera calibration procedure with implicit image correction; Proceedings IEEE Computer Scociety Conference on Computer Vision and Pattern Recognition; San Juan; pp. 1106-1112; Jun. 17-19, 1997.
Hendee et al.; Medical Imaging Physics; Wiley-Liss, Inc. 4th Edition; Chap. 19-22; pp. 303-353; (year of pub. sufficiently earlier than effective US filing date and any foreign priority date) © 2002.

Hsu et al.; Real-time freehand 3D ultrasound calibration; CUED/F-INFENG/TR 565; Department of Engineering, University of Cambridge, United Kingdom; 14 pages; Sep. 2006.
Jeffs; Beamforming: a brief introduction; Brigham Young University; 14 pages; retrieved from the internet (http://ens.ewi.tudelft.nl/Education/courses/et4235/Beamforming.pdf); Oct. 2004.
Khamene et al.; A novel phantom-less spatial and temporal ultrasound calibration method; Medical Image Computing and Computer-Assisted Intervention—MICCAI (Proceedings 8th Int. Conf.); Springer Berlin Heidelberg; Palm Springs, CA; pp. 65-72; Oct. 26-29, 2005.
Kramb et al.,.; Considerations for using phased array ultrasonics in a fully automated inspection system. Review of Quantitative Nondestructive Evaluation, 2004 Edition, ed. D. O. Thompson and D. E. Chimenti, American Inst. of Physics, pp. 817-825, Mar. 2004.
Ledesma-Carbayo et al.; Spatio-temporal nonrigid registration for ultrasound cardiac motion estimation; IEEE Trans. On Medical Imaging; vol. 24; No. 9; Sep. 2005.
Leotta et al.; Quantitative three-dimensional echocardiography by rapid imaging . . . ; J American Society of Echocardiography; vol. 10; No. 8; pp. 830-839; Oct. 1997.
Li et al.; An efficient speckle tracking algorithm for ultrasonic imaging; 24; pp. 215-228; Oct. 1, 2002.
Montaldo et al.; Building three-diminisional images using a time-reversal chaotic cavity; IEEE Trans. on Ultrasonics, Ferroelectrics, and Frequency Control; 52(9); pp. 1489-1497; Sep. 2005.
Morrison et al.; A probabilistic neural network based image segmentation network for magnetic resonance images; Proc. Conf. Neural Networks; Baltimore, MD; vol. 3; pp. 60-65; Jun. 1992.
Nadkarni et al.; Cardiac motion synchronization for 3D cardiac ultrasound imaging; Ph.D. Dissertation, University of Western Ontario; Jun. 2002.
Press et al.; Cubic spline interpolation; §3.3 in "Numerical Recipes in FORTRAN: The Art of Scientific Computing", 2nd Ed.; Cambridge, England; Cambridge University Press; pp. 107-110; Sep. 1992.
Saad et al.; Computer vision approach for ultrasound doppler angle estimation; Journal of Digital Imaging; 22(6); pp. 681-688; Dec. 1, 2009.
Sakas et al.; Preprocessing and volume rendering of 3D ultrasonic data; IEEE Computer Graphics and Applications; pp. 47-54, Jul. 1995.
Sapia et al.; Deconvolution of ultrasonic waveforms using an adaptive wiener filter; Review of Progress in Quantitative Nondestructive Evaluation; vol. 13A; Plenum Press; pp. 855-862; Jan. 1994.
Sapia et al.; Ultrasound image deconvolution using adaptive inverse filtering; 12 IEEE Symposium on Computer-Based Medical Systems, CBMS, pp. 248-253; Jun. 1999.
Sapia, Mark Angelo; Multi-dimensional deconvolution of optical microscope and ultrasound imaging using adaptive least-mean-square (LMS) inverse filtering; Ph.D. Dissertation; University of Connecticut; Jan. 2000.
Scabia et al.; A real-time two-dimensional pulsed-wave Doppler system; Ultrasound in medicine & biology: 26(1); pp. 121-131; Jan. 1, 2000.
Slavine et al.; Construction, calibration and evaluation of a tissue phantom with reproducible optical properties for investigations in light emission tomography; Engineering in Medicine and Biology Workshop; Dallas, TX; IEEE pp. 122-125; Nov. 11-12, 2007.
Smith et al.; High-speed ultrasound volumetric imaging system. 1. Transducer design and beam steering; IEEE Trans. Ultrason., Ferroelect., Freq. Contr.; vol. 38; pp. 100-108; Mar. 1991.
Specht et al.; Deconvolution techniques for digital longitudinal tomography; SPIE; vol. 454; presented at Application of Optical Instrumentation in Medicine XII; pp. 319-325; Jun. 1984.
Specht et al.; Experience with adaptive PNN and adaptive GRNN; Proc. IEEE International Joint Conf. on Neural Networks; vol. 2; pp. 1203-1208; Orlando, FL; Jun. 1994.
Specht, D.F.; A general regression neural network; IEEE Trans. On Neural Networks; vol. 2.; No. 6; Nov. 1991.
Specht, D.F.; Blind deconvolution of motion blur using LMS inverse filtering; Lockheed Independent Research (unpublished); Jun. 23, 1975.

(56) References Cited

OTHER PUBLICATIONS

Specht, D.F.; Enhancements to probabilistic neural networks; Proc. IEEE International Joint Conf. on Neural Networks; Baltimore, MD; Jun. 1992.

Specht, D.F.; GRNN with double clustering; Proc. IEEE International Joint Conf. Neural Networks; Vancouver, Canada; Jul. 16-21, 2006.

Specht, D.F.; Probabilistic neural networks; Pergamon Press; Neural Networks; vol. 3; pp. 109-118; Feb. 1990.

Stern; The basic concepts of diagnostic ultrasound. Yale-New Haven Teachers Institute; Apr. 2005.

UCLA Academic Technology; SPSS learning module: How can I analyze a subset of my data; 6 pages; retrieved from the internet (http://www.ats.ucla.edu/stat/spss/modules/subset_analyze.htm) Nov. 26, 2001.

Urban et al.; Implementation of vibro-acoustography on a clinical ultrasound system; IEEE Ultrasonics Symposium (IUS); pp. 326-329; Oct. 14, 2010.

Von Ramm et al.; High-speed ultrasound volumetric imaging—System. 2. Parallel processing and image display; IEEE Trans. Ultrason., Ferroelect., Freq. Contr.; vol. 38; pp. 109-115; Mar. 1991.

Wang et al.; Photoacoustic tomography of biological tissues with high cross-section resolution: reconstruction and experiment; Medical Physics; 29(12); pp. 2799-2805; Dec. 2002.

Wells, P.N.T.; Biomedical ultrasonics; Academic Press; London, New York, San Francisco; pp. 124-125; Mar. 1977.

Widrow et al.; Adaptive signal processing; Prentice-Hall; Englewood Cliffs, NJ; pp. 99-116; Mar. 1985.

Wikipedia; Point cloud; 2 pages; retrieved Nov. 24, 2014 from the internet (https://en.wikipedia.org/w/index.php?title=Point_cloud&oldid=472583138).

Wikipedia; Curve fitting; 5 pages; retrieved from the internet (http:en.wikipedia.org/wiki/Curve_fitting) Dec. 19, 2010.

Wikipedia; Speed of sound; 17 pages; retrieved from the internet (http:en.wikipedia.org/wiki/Speed_of_sound) Feb. 15, 2011.

Yang et al.; Time-of-arrival calibration for improving the microwave breast cancer imaging; 2011 IEEE Topical Conf. on Biomedical Wireless Technologies, Networks, and sensing Systems (BioWireleSS); Phoenix, AZ; pp. 67-70; Jan. 16-19, 2011.

Zhang et al.; A high-frequency high frame rate duplex ultrasound linear array imaging system for small animal imaging; IEEE transactions on ultrasound, ferroelectrics, and frequency control; 57(7); pp. 1548-1567; Jul. 2010.

Bajikar et al.; U.S. Appl. No. 18/165,276 entitled "Multiple aperture ultrasound imaging systems and methods," filed Feb. 6, 2023.

Jensen et al.; Synthetic aperture ultrasound imaging; Ultrasonics; vol. 44, pp. e5-e15; Dec. 22, 2006.

Call et al.; U.S. Appl. No. 18/330,699 entitled "Network-based ultrasound imaging system," filed Jun. 7, 2023.

Atmeh et al.; U.S. Appl. No. 18/251,421 entitled "Systems and methods for improving ultrasound image quality," filed May 2, 2023.

Smith et al.; U.S. Appl. No. 18/344,278 entitled "Concave ultrasound transducers and 3d arrays," filed Jun. 29, 2023.

Call et al.; U.S. Appl. No. 18/344,479 entitled "Ultrasound imaging systems and methods for detecting object motion," filed Jun. 29, 2023.

Lockwood et al.; Real-time 3-D ultrasound imaging using sparse synthetic aperture beamforming; IEEE transactions on ultrasonics, ferroelectrics, and frequency control; 45(4); pp. 980-988, Jul. 1998.

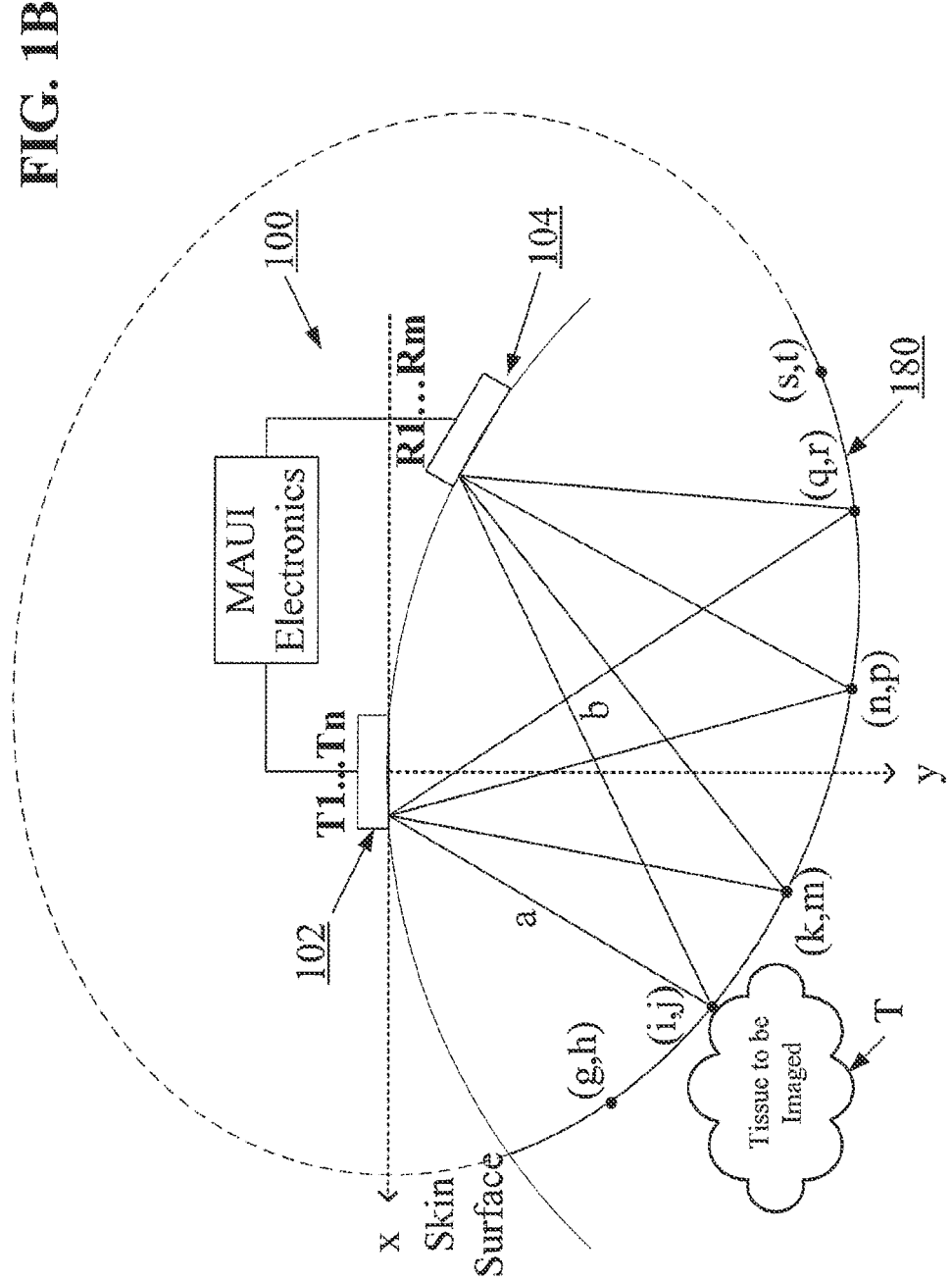

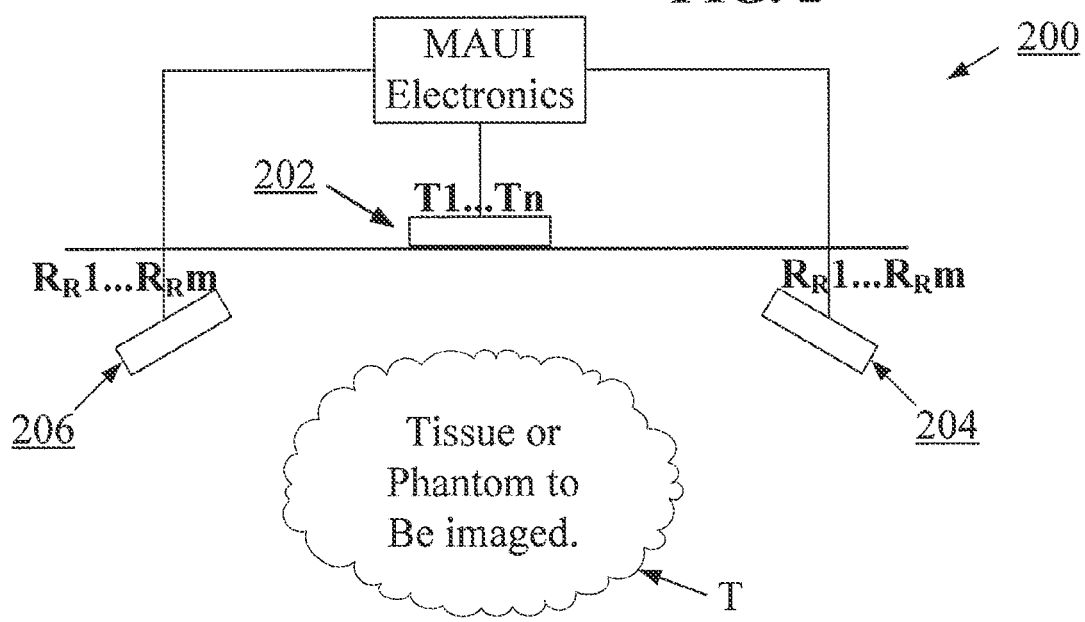

POINT SOURCE TRANSMISSION AND SPEED-OF-SOUND CORRECTION USING MULTI-APERTURE ULTRASOUND IMAGING

CROSS REFERENCE TO RELATED APPLICATIONS

This application is a continuation of U.S. application Ser. No. 16/506,570, filed Jul. 9, 2019, which is a continuation of U.S. application Ser. No. 16/000,507, filed Jun. 5, 2018, now U.S. Pat. No. 10,342,518, which is a continuation of U.S. application Ser. No. 15/364,075, filed Nov. 29, 2016, now U.S. Pat. No. 9,986,975, which is a continuation of U.S. application Ser. No. 14/846,374, filed Sep. 4, 2015, now U.S. Pat. No. 9,526,475, which is a continuation of U.S. application Ser. No. 13/029,907, filed Feb. 17, 2011, now U.S. Pat. No. 9,146,313, which application claims the benefit of U.S. Provisional Application No. 61/305,784, filed Feb. 18, 2010, entitled "Alternative Method for Medical Multi-Aperture Ultrasound Imaging".

This application is also related to U.S. application Ser. No. 11/865,501, filed Oct. 1, 2007, now U.S. Pat. No. 8,007,439, titled "Method and Apparatus to Produce Ultrasonic Images Using Multiple Apertures", and to U.S. application Ser. No. 11/532,013, filed Sep. 14, 2006, now U.S. Pat. No. 8,105,239, titled "Method and Apparatus to Visualize the Coronary Arteries Using Ultrasound"; all of which are herein incorporated by reference in their entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

BACKGROUND OF THE INVENTION

In conventional ultrasonic imaging, a focused beam of ultrasound energy is transmitted into body tissues to be examined and the returned echoes are detected and plotted to form an image. The basic principles of conventional ultrasonic imaging are well described in the first chapter of "Echocardiography," by Harvey Feigenbaum (Lippincott Williams & Wilkins, 5th ed., Philadelphia, 1993).

In order to insonify body tissues, an ultrasound beam is typically formed and focused either by a phased array or a shaped transducer. Phased array ultrasound is a commonly used method of steering and focusing a narrow ultrasound beam for forming images in medical ultrasonography. A phased array probe has many small ultrasonic transducer elements, each of which can be pulsed individually. By varying the timing of ultrasound pulses (e.g., by pulsing elements one by one in sequence along a row), a pattern of constructive interference is set up that results in a beam directed at a chosen angle. This is known as beam steering. Such a steered ultrasound beam may then be swept through the tissue or object being examined. Data from multiple beams are then combined to make a visual image showing a slice through the object.

Traditionally, the same transducer or array used for transmitting an ultrasound beam is used to detect the returning echoes. This design configuration lies at the heart of one of the most significant limitations in the use of ultrasonic imaging for medical purposes: poor lateral resolution. Theoretically, the lateral resolution could be improved by increasing the width of the aperture of an ultrasonic probe, but practical problems involved with aperture size increase have kept apertures small. Unquestionably, ultrasonic imaging has been very useful even with this limitation, but it could be more effective with better resolution.

In the practice of cardiology, for example, the limitation on single aperture size is dictated by the space between the ribs (the intercostal spaces). Such intercostal apertures are typically limited to no more than about one to two centimeters. For scanners intended for abdominal and other use, the limitation on aperture size is less a matter of physical constraints, and more a matter of difficulties in image processing. The problem is that it is difficult to keep the elements of a large aperture array in phase because the speed of ultrasound transmission varies with the type of tissue between the probe and the area of interest. According to the book by Wells (cited above), the speed varies up to plus or minus 10% within the soft tissues. When the aperture is kept small (e.g., less than about 2 cm), the intervening tissue is, to a first order of approximation, all the same and any variation is ignored. When the size of the aperture is increased to improve the lateral resolution, the additional elements of a phased array may be out of phase and may actually degrade the image rather than improving it.

US Patent Publication 2008/0103393, now U.S. Pat. No. 8,007,439, to Specht teaches embodiments of ultrasound imaging systems utilizing multiple apertures which may be separated by greater distances, thereby producing significant improvements in lateral resolution of ultrasound images.

SUMMARY OF THE INVENTION

One embodiment of a method describes a method of constructing an ultrasound image, comprising transmitting an omni-directional unfocused ultrasound waveform approximating a first point source within a transmit aperture on a first array through a target region, receiving ultrasound echoes from the target region with first and second receiving elements disposed on a first receive aperture on a second array, the first array being physically separated from the second array, determining a first time for the waveform to propagate from the first point source to a first pixel location in the target region to the first receiving element, and determining a second time for the waveform to propagate from the first point source to the first pixel location in the target region to the second receiving element, and forming a first ultrasound image of the first pixel by combining the echo received by the first receiving element at the first time with the echo received by the second receiving element at the second time.

In some embodiments, the method further comprises repeating the determining and forming steps for additional pixel locations in the target region. In one embodiment, additional pixel locations are located on a grid without scan-conversion.

In one embodiment, determining the first time and the second time comprises assuming a uniform speed of sound.

In another embodiment, the method further comprises transmitting a second omni-directional unfocused ultrasound waveform approximating a second point source within the transmit aperture through the target region, receiving ultrasound echoes from the target region with first and second receiving elements disposed on the first receive aperture, determining a third time for the second waveform to propagate from the second point source to the first pixel location in the target region to the first receiving element, and determining a fourth time for the second waveform to propagate from the second point source to the first pixel location in the target region to the second receiving element, and forming a second ultrasound image of the first pixel by combining the echo received by the first receiving element at the third time with the echo received by the second receiving element at the fourth time.

In some embodiments, the method further comprises combining the first ultrasound image with the second ultrasound image. The combining step can comprise coherent addition. In another embodiment, the combining step can comprise incoherent addition. In yet another embodiment, the combining step can comprise a combination of coherent addition and incoherent addition.

In some embodiments, the method can further comprise receiving ultrasound echoes from the target region with third and fourth receiving elements disposed on a second receive aperture on a third array, the third array being physically separated from the first and second arrays, determining a third time for the waveform to propagate from the first point source to the first pixel location in the target region to the third receiving element, and determining a fourth time for the waveform to propagate from the first point source to the first pixel location in the target region to the fourth receiving element, and forming a second ultrasound image of the first pixel by combining the echo received by the third receiving element at the third time with the echo received by the fourth receiving element at the fourth time.

In some embodiments, the method further comprises repeating the determining and forming steps for additional pixel locations in the target region. In some embodiments, the additional pixel locations are located on a grid without scan-conversion.

In one embodiment, the method further comprises transmitting a second omni-directional unfocused ultrasound waveform approximating a second point source within the transmit aperture through the target region, receiving ultrasound echoes from the target region with first and second receiving elements disposed on the first receive aperture and with the third and fourth receiving elements disposed on the second receive aperture, determining a fifth time for the second waveform to propagate from the second point source to the first pixel location in the target region to the first receiving element, determining a sixth time for the second waveform to propagate from the second point source to the first pixel location in the target region to the second receiving element, determining a seventh time for the second waveform to propagate from the second point source to the first pixel location in the target region to the third receiving element, determining an eighth time for the second waveform to propagate from the second point source to the first pixel location in the target region to the fourth receiving element, and forming a third ultrasound image of the first pixel by combining the echo received by the first receiving element at the fifth time with the echo received by the second receiving element at the sixth time, and forming a fourth ultrasound image of the first pixel by combining the echo received by the third receiving element at the seventh time with the echo received by the fourth receiving element at the eighth time.

In some embodiments, the method further comprises combining the first, second, third, and fourth ultrasound images. In some embodiments, the combining step comprises coherent addition. In other embodiments, the combining step comprises incoherent addition. In additional embodiments, the combining step comprises a combination of coherent addition and incoherent addition.

In some embodiments, the method comprises combining the first ultrasound image with the second ultrasound image. The combining step can comprise coherent addition. In another embodiment, the combining step can comprise incoherent addition. In yet another embodiment, the combining step can comprise a combination of coherent addition and incoherent addition.

In some embodiments, the method further comprises comparing the first ultrasound image to the second, third, and fourth ultrasound images to determine displacements of the second, third, and fourth ultrasound images relative to the first ultrasound image.

In another embodiment, the method further comprises correcting the displacements of the second, third, and fourth ultrasound images relative to the first ultrasound image and then combining the first, second, third and fourth ultrasound images.

In an additional embodiment, the method comprises adjusting the third, fourth, fifth, sixth, seventh, and eighth times to correct the displacements of the second, third, and fourth ultrasound images relative to the first ultrasound image.

In some embodiments, the method further comprises comparing the first ultrasound image to the second ultrasound image to determine a displacement of the second ultrasound image relative to the first ultrasound image.

The method can further comprise correcting the displacement of the second ultrasound image relative to the first ultrasound image and then combining the first and second ultrasound images.

In another embodiment, the method comprises adjusting the third time and the fourth time to correct the displacement of the second ultrasound image relative to the first ultrasound image.

In some embodiments, the first pixel is disposed outside a plane defined by the point source, the first receiving element, and the second receiving element. In other embodiments, the first pixel is disposed inside a plane defined by the point source, the first receiving element, and the second receiving element.

Various embodiments of a multi-aperture ultrasound imaging system are also provided, comprising a transmit aperture on a first array configured to transmit an omni-directional unfocused ultrasound waveform approximating a first point source through a target region, a first receive aperture on a second array having first and second receiving elements, the second array being physically separated from the first array, wherein the first and second receiving elements are configured to receive ultrasound echoes from the target region, and a control system coupled to the transmit aperture and the first receive aperture, the control system configured to determine a first time for the waveform to propagate from the first point source to a first pixel location in the target region to the first receiving element, and is configured to determine a second time for the waveform to propagate from the first point source to the first pixel location in the target region to the second receiving element, the control system also being configured to form a first ultrasound image of the first pixel by combining the echo received by the first receiving element at the first time with the echo received by the second receiving element at the second time.

In some embodiments of the system, there are no transducer elements disposed between the physical separation of the transmit aperture and the first receive aperture.

In one embodiment of the system, the transmit aperture and the first receive aperture are separated by at least twice a minimum wavelength of transmission from the transmit aperture. In another embodiment, the transmit aperture and the receive aperture comprise a total aperture ranging from 2 cm to 10 cm.

In some embodiments, the ultrasound system further comprises a second receive aperture on a third array having third and fourth receiving elements, the third array being physically separated from the first and second arrays, wherein the third and fourth receiving elements are configured to receive ultrasound echoes from the target region.

In another embodiment of the multi-aperture ultrasound imaging system, the control system can be coupled to the transmit aperture and the first and second receive apertures, wherein the control system is configured to determine a third time for the waveform to propagate from the first point source to a first pixel location in the target region to the third receiving element, and is configured to determine a fourth time for the waveform to propagate from the first point source to the first pixel location in the target region to the fourth receiving element, the control system also being configured to form a second ultrasound image of the first pixel by combining the echo received by the third receiving element at the third time with the echo received by the fourth receiving element at the fourth time.

In some embodiments, the control system is configured to correct a displacement of the second ultrasound image relative to the first ultrasound image due to speed of sound variation.

In other embodiments of the multi-aperture ultrasound imaging system, the transmit aperture, the first receive aperture, and the second receive aperture are not all in a single scan plane.

BRIEF DESCRIPTION OF THE DRAWINGS

FIG. 1B: Equidistant time delay points forming an ellipse around a transmit transducer element and receive transducer element.
FIG. 2: A three-aperture system.

DETAILED DESCRIPTION OF THE INVENTION

Greatly improved lateral resolution in ultrasound imaging can be achieved by using multiple separate apertures for transmit and receive functions. Systems and methods herein may provide for both transmit functions from point sources and for compensation for variations in the speed-of-sound of ultrasound pulses traveling through potentially diverse tissue types along a path between a transmit aperture and one or more receive apertures. Such speed-of-sound compensation may be performed by a combination of image comparison techniques (e.g., cross-correlation), and the coherent and/or incoherent averaging of a plurality of received image frames.

As used herein the terms "ultrasound transducer" and "transducer" may carry their ordinary meanings as understood by those skilled in the art of ultrasound imaging technologies, and may refer without limitation to any single component capable of converting an electrical signal into an ultrasonic signal and/or vice versa. For example, in some embodiments, an ultrasound transducer may comprise a piezoelectric device. In some alternative embodiments, ultrasound transducers may comprise capacitive micromachined ultrasound transducers (CMUT). Transducers are often configured in arrays of multiple elements. An element of a transducer array may be the smallest discrete component of an array. For example, in the case of an array of piezoelectric transducer elements, each element may be a single piezoelectric crystal.

As used herein, the terms "transmit element" and "receive element" may carry their ordinary meanings as understood by those skilled in the art of ultrasound imaging technologies. The term "transmit element" may refer without limitation to an ultrasound transducer element which at least momentarily performs a transmit function in which an electrical signal is converted into an ultrasound signal. Similarly, the term "receive element" may refer without limitation to an ultrasound transducer element which at least momentarily performs a receive function in which an ultrasound signal impinging on the element is converted into an electrical signal. Transmission of ultrasound into a medium may also be referred to herein as "insonifying." An object or structure which reflects ultrasound waves may be referred to as a "reflector" or a "scatterer."

Figure 3:
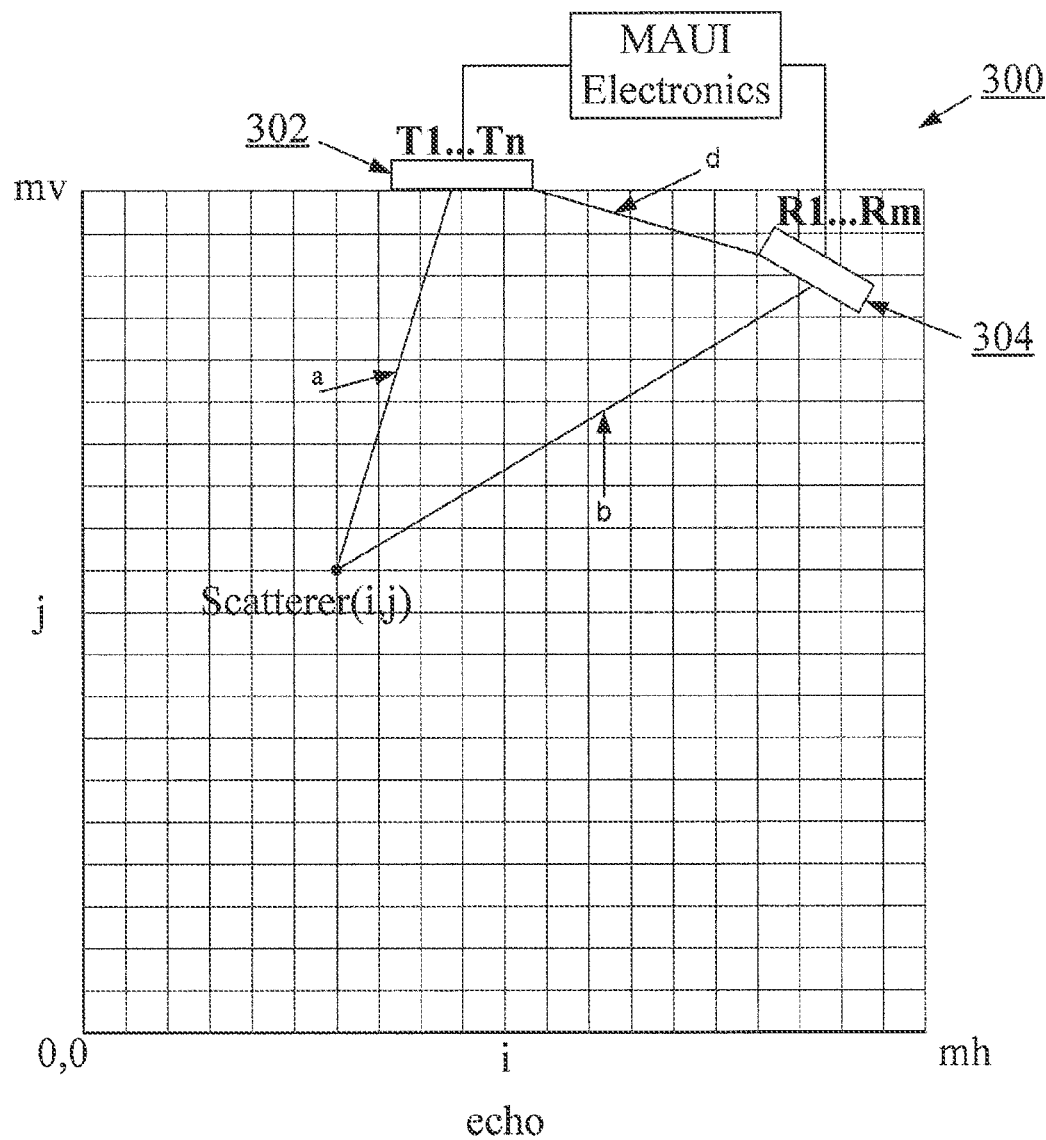
FIG. 3: Grid for display and coordinate system.

As used herein the term "aperture" refers without limitation to one or more ultrasound transducer elements collectively performing a common function at a given instant of time. For example, in some embodiments, the term aperture may refer to a group of transducer elements performing a transmit function. In alternative embodiments, the term aperture may refer to a plurality of transducer elements performing a receive function. In some embodiments, group of transducer elements forming an aperture may be redefined at different points in time. FIG. 3 demonstrates multiple apertures used in a multiple aperture ultrasound probe. An aperture of the probe has up to three distinct features. First, it is often physically separated from other transducers located in other apertures. In FIG. 3, a distance 'd' physically separates aperture 302 from aperture 304. Distance 'd' can be the minimum distance between transducer elements on aperture 302 and transducer elements on aperture 304. In some embodiments, no transducer elements are disposed along the distance between the physical separation of apertures 302 and 304. In some embodiments, the distance 'd' can be equal to at least twice the minimum wavelength of transmission from the transmit aperture. Second, the transducer elements of an aperture need not be in the same rectangular or horizontal plane. In FIG. 3, all the elements of aperture 304 have a different vertical position 'j' from any element of aperture 302. Third, apertures do not share a common line of sight to the region of interest. In FIG. 3, aperture 302 has a line of sight 'a' for point (i,j), while aperture 304 has a line of sight 'b'. An aperture may include any number of individual ultrasound elements. Ultrasound elements defining an aperture are often, but not necessarily adjacent to one another within an array. During operation of a multi-aperture ultrasound imaging system, the size of an aperture (e.g., the number and/or size and/or position of ultrasound elements) may be dynamically changed by re-assigning elements.

As used herein the term "point source transmission" may refer to an introduction of transmitted ultrasound energy into a medium from single spatial location. This may be accomplished using a single ultrasound transducer element or combination of adjacent transducer elements transmitting together. A single transmission from said element(s)

approximates a uniform spherical wave front, or in the case of imaging a 2D slice it creates a uniform circular wave front within the 2D slice. This point source transmission differs in its spatial characteristics from a "phased array transmission" which focuses energy in a particular direction from the transducer element array. Phased array transmission manipulates the phase of a group of transducer elements in sequence so as to strengthen or steer an insonifying wave to a specific region of interest. A short duration point source transmission is referred to herein as a "point source pulse." Likewise, a short duration phased array transmission is referred to herein as a "phased array pulse."

As used herein, the terms "receive aperture," "insonifying aperture," and/or "transmit aperture" can carry their ordinary meanings as understood by those skilled in the art of ultrasound imaging, and may refer to an individual element, a group of elements within an array, or even entire arrays within a common housing, that perform the desired transmit or receive function from a desired physical viewpoint or aperture at a given time. In some embodiments, these various apertures may be created as physically separate components with dedicated functionality. In alternative embodiments, the functionality may be electronically designated and changed as needed. In still further embodiments, aperture functionality may involve a combination of both fixed and variable elements.

In some embodiments, an aperture is an array of ultrasound transducers which is separated from other transducer arrays. Such multiple aperture ultrasound imaging systems provide greatly increased lateral resolution. According to some embodiments, a multi-aperture imaging method comprises the steps of insonifying a target object with an ultrasound pulse from a first aperture, detecting returned echoes with a second aperture positioned at a distance from the first aperture, determining the relative positions of the second aperture with respect to the first aperture, and processing returned echo data to combine images while correcting for variations in speed-of-sound through the target object.

In some embodiments, a distance and orientation between adjacent apertures may be fixed relative to one another, such as by use of a rigid housing. In alternative embodiments, distances and orientations of apertures relative to one another may be variable, such as with a movable linkage. In further alternative embodiments, apertures may be defined as groups of elements on a single large transducer array where the groups are separated by at least a specified distance. For example, some embodiments of such a system are shown and described in U.S. Provisional Application No. 61/392,896, filed Oct. 13, 2010, titled "Multiple Aperture Medical Ultrasound Transducers". In some embodiments of a multi-aperture ultrasound imaging system, a distance between adjacent apertures may be at least a width of one transducer element. In alternative embodiments, a distance between apertures may be as large as possible within the constraints of a particular application and probe design.

A multi-aperture ultrasound imaging system with a large effective aperture (the total aperture of the several sub apertures) can be made viable by compensation for the variation of speed-of-sound in the target tissue. This may be accomplished in one of several ways to enable the increased aperture to be effective rather than destructive, as described below.

Figure 1A:
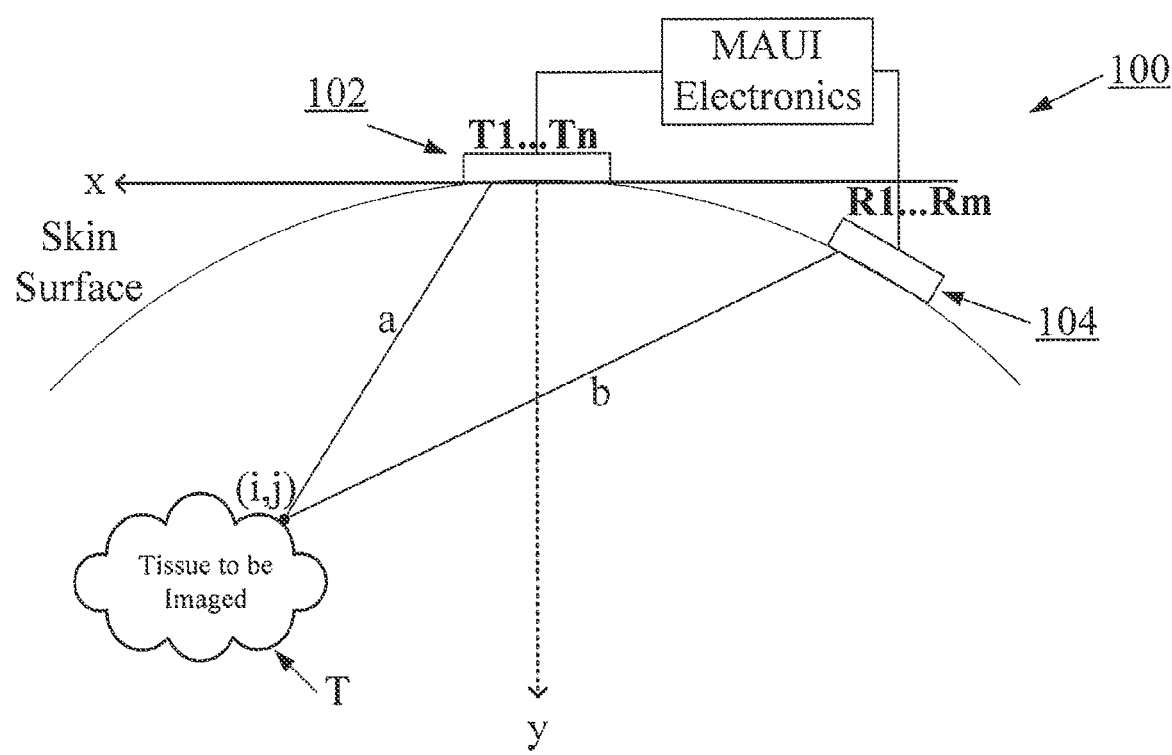
FIG. 1A: A two-aperture system.

FIG. 1A illustrates one embodiment of a simplified multi-aperture ultrasound imaging system 100 comprising two apertures, aperture 102 and aperture 104. Each of apertures 102 and 104 can comprise a plurality of transducer elements.

In the two-aperture system shown in FIG. 1A, aperture 102 can comprise transmit elements T1 . . . Tn to be used entirely for transmit functions, and aperture 104 can comprise receive elements R1 . . . Rm to be used entirely for receive functions. In alternative embodiments, transmit elements may be interspersed with receive elements, or some elements may be used both for transmit and receive functions. The multi-aperture ultrasound imaging system 100 of FIG. 1A can be configured to be placed on a skin surface of a patient to image target object or internal tissue T with ultrasound energy. As shown in FIG. 1A, aperture 102 is positioned a distance "a" from tissue T, and aperture 104 is positioned a distance "b" from tissue T. Also shown in FIG. 1A, MAUI electronics may be coupled to the transmit and receive apertures 102 and 104. In some embodiments, the MAUI electronics can comprise a processor, control system, or computing system, including hardware and software configured to control the multi-aperture imaging system 100. In some embodiments, the MAUI electronics can be configured to control the system to transmit an omni-directional unfocused ultrasound waveform from an aperture, receive echoes on an aperture, and form images from the transmitted waveform and the received echoes. As will be described in further detail below, the MAUI electronics can be configured to control and achieve any of the methods described herein.

Ultrasound elements and arrays described herein may also be multi-function. That is, the designation of transducer elements or arrays as transmitters in one instance does not preclude their immediate re-designation as receivers in the next instance. Moreover, embodiments of the control system described herein include the capabilities for making such designations electronically based on user inputs or pre-set scan or resolution criteria.

Another embodiment of a multi-aperture ultrasound imaging system 200 is shown in FIG. 2 and includes transducer elements arranged to form three apertures 202, 204, and 206. In one embodiment, transmit elements T1 . . . Tn in aperture 202 may be used for transmit, and receive elements $R_R1$ . . . $R_Rm$ in apertures 204 and 206 may be used for receive. In alternative embodiments, elements in all the apertures may be used for both transmit and receive. The multi-aperture ultrasound imaging system 200 of FIG. 2 can be configured to image tissue T with ultrasound energy. Also shown in FIG. 2, MAUI electronics may be coupled to the transmit and receive apertures 202 and 204. In some embodiments, the MAUI electronics can comprise a processor, control system, or computing system, including hardware and software configured to control the multi-aperture imaging system 200. In some embodiments, the MAUI electronics can be configured to control the system to transmit an omni-directional unfocused ultrasound waveform from an aperture, receive echoes on an aperture, and form images from the transmitted waveform and the received echoes. As will be described in further detail below, the MAUI electronics can be configured to control and achieve any of the methods described herein.

Multi-aperture ultrasound imaging systems described herein may be configured to utilize transducers of any desired construction. For example, 1D, 1.5D, 2D, CMUT or any other transducer arrays may be utilized in multi-aperture configurations to improve overall resolution and field of view.

Point Source Transmission

In some embodiments, acoustic energy may be transmitted to as wide a two-dimensional slice as possible by using point source transmission. For example, in some embodiments, a transmit aperture, such as transmit apertures 102 or 202 in FIGS. 1A and 2, respectively, may transmit acoustic energy in the form of a point source pulse from a single substantially omni-directional transducer element in an array. In alternative embodiments, a plurality of transducer elements may be provisioned to transmit a point source pulse that is relatively wide in three dimensions to insonify objects in a three dimensional space. In such embodiments, all of the beam formation may be achieved by the software or firmware associated with the transducer arrays acting as receivers. There are several advantages to using a multi-aperture ultrasound imaging technique by transmitting with a point source pulse rather than a phased array pulse. For example when using a phased array pulse, focusing tightly on transmit is problematic because the transmit pulse would have to be focused at a particular depth and would be somewhat out of focus at all other depths. Whereas, with a point source transmission an entire two-dimensional slice or three-dimensional volume can be insonified with a single point source transmit pulse.

Each echo detected at a receive aperture, such as receive apertures 104 or 204/206 in FIGS. 1A and 2, respectively, may be stored separately. If the echoes detected with elements in a receive aperture are stored separately for every point source pulse from an insonifying or transmit aperture, an entire two-dimensional image can be formed from the information received by as few as just one element. Additional copies of the image may be formed by additional receive apertures collecting data from the same set of insonifying point source pulses. Ultimately, multiple images can be created simultaneously from one or more apertures and combined to achieve a comprehensive 2D or 3D image.

Although several point source pulses are typically used in order to produce a high-quality image, fewer point source pulses are required than if each pulse were focused on a particular scan line. Since the number of pulses that can be transmitted in a given time is strictly limited by the speed of ultrasound in tissue, this yields the practical advantage that more frames can be produced per second by utilizing a point source pulse. This is very important when imaging moving organs, and in particular, the heart.

In some embodiments, a spread spectrum waveform may be imposed on a transmit aperture made up of one or more ultrasound transducer elements. A spread spectrum waveform may be a sequence of frequencies such as a chirp (e.g., frequencies progressing from low to high, or vice versa), random frequency sequence (also referred to as frequency hop), or a signal generated by a pseudo random waveform (PN sequence). These techniques can be collectively referred to as pulse compression. Pulse compression provides longer pulses for greater depth penetration without loss of depth resolution. In fact, the depth resolution may be greatly improved in the process. Spread spectrum processing typically involves much more signal processing in the form of matched filtering of each of the received signals before the delay and summation steps. The above examples of transmit pulse forms are provided for illustration only. The techniques taught herein may apply regardless of the form of the transmit pulse.

Basic Image Rendering

FIG. 1A illustrates one embodiment of a multi-aperture ultrasound imaging system 100 containing a first aperture 102 with ultrasound transmitting elements T1, T2, . . . Tn and a second aperture 104 with ultrasound receive elements R1, R2, . . . Rm. This multi-aperture ultrasound imaging system 100 is configured to be placed on the surface of an object or body to be examined (such as a human body). In some embodiments, both apertures may be sensitive to the same plane of scan. In other embodiments, one of the apertures may be in a different plane of scan. The mechanical and acoustic position of each transducer element of each aperture must be known precisely relative to a common reference point or to each other.

In one embodiment, an ultrasound image may be produced by insonifying the entire region to be imaged, such as internal tissue or target object T, (e.g., a plane through the heart, organ, tumor, or other portion of the body) with a transmitting element (e.g., transmit element T1 of aperture 102), and then receiving echoes from the entire imaged plane on a receive element (e.g., receive element R1 of aperture 104). In some embodiments, receive functions may be performed by all elements in the receive probe (e.g., R1 through Rm). In alternative embodiments, echoes are received on only one or a select few elements of the receive aperture. The method proceeds by using each of the elements on the transmitting aperture 102 (e.g., T2, . . . Tn) and insonifying the entire region to be imaged with each of the transmitting elements in turn, and receiving echoes on the receive aperture after each insonifying pulse. Transmit elements may be operated in any desired sequential order, and need not follow a prescribed pattern. Individually, the images obtained after insonification by each transmitting element may not be sufficient to provide a high resolution image, but the combination of all the images may provide a high resolution image of the entire region to be imaged. For a scanning point represented by coordinates (i,j) as shown in FIG. 1A, it is a simple matter to calculate the total distance "a" from a particular transmit element Tx to an element of internal tissue or target object T at (i,j), and the distance "b" from that point to a particular receive element. These calculations may be performed using basic trigonometry. The sum of these distances is the total distance traveled by one ultrasound wave.

When the speed of ultrasound in tissue is assumed to be uniform throughout the tissue, it is possible to calculate the time delay from the onset of the transmit pulse to the time that an echo is received at the receive element. (Non uniform speed-of-sound in tissue is discussed below.) This one fact means that a scatterer (i.e., a reflective point within the target object) is a point in the medium for which a+b=the given time delay. The same method can be used to calculate delays for any point in the desired tissue to be imaged, creating a locus of points. FIG. 1B demonstrates that points (g,h), (i,j), (k,m), (n,p) (q,r), (s,t) all have the same time delay for transmit element $T_1$ and receive element $R_1$. A map of scatter positions and amplitudes can be rendered by tracing the echo amplitude to all of the points for the locus of equal-time-delay points. This locus takes the form of an ellipse 180 with foci at the transmit and receive elements. FIG. 1B also illustrates MAUI electronics, which can comprise the MAUI electronics described above with reference to FIGS. 1A and 2.

The fact that all points on the ellipse 180 are returned with the same time delay presents a display challenge, since distinguishing points along the ellipse from one another within a single image is not possible. However, by combining images obtained from multiple receive points, the points may be more easily distinguished, since the equal-time-delay ellipses defined by the multiple receive apertures will be slightly different.

Figure 1C:
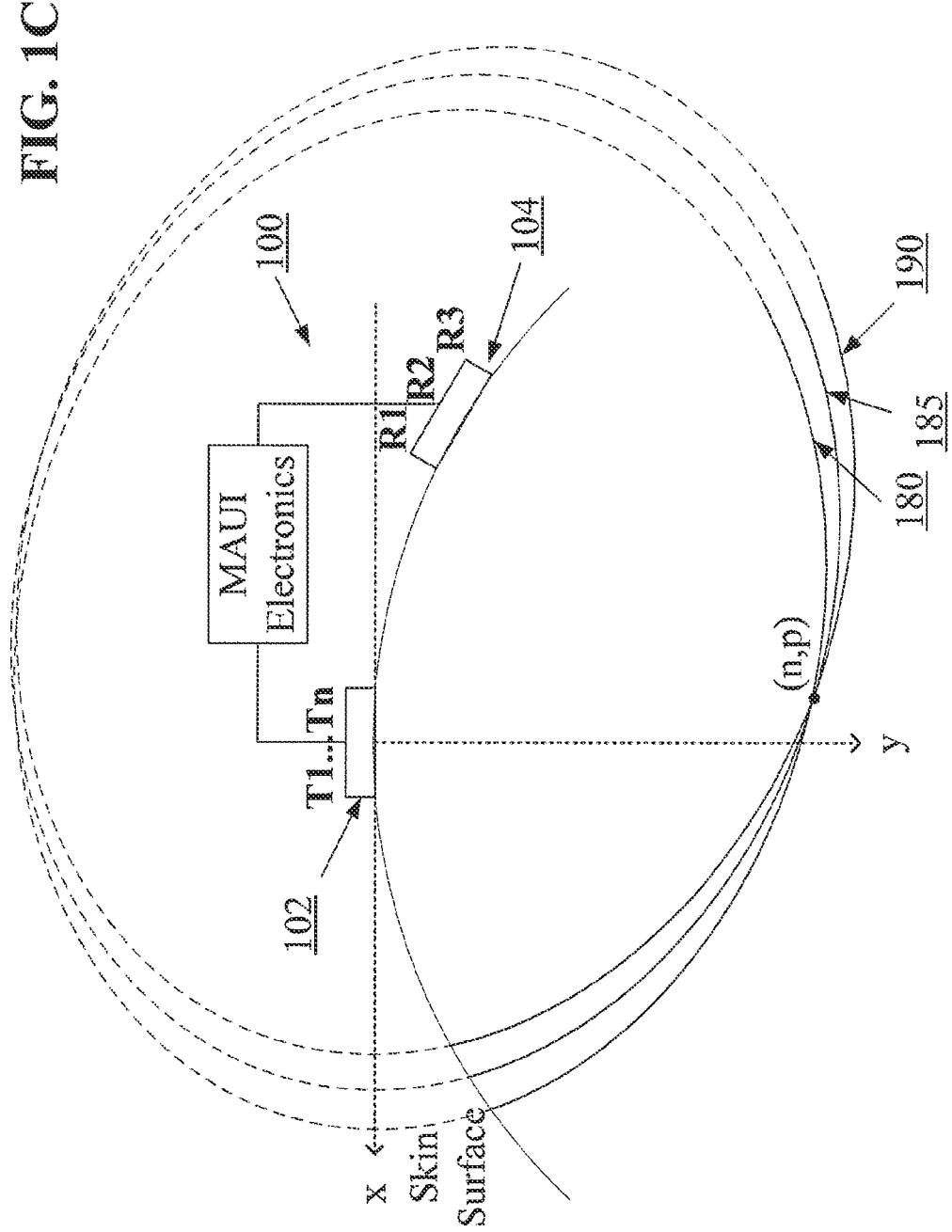
FIG. 1C: Loci of points relative to equidistant time delays for different receive transducer elements.

FIG. 1C shows that with a transmit pulse from element T1, echoes from a single scatterer (n,p) are received by different receive elements such as R1, R2, and R3 at different times. The loci of the same scatterer can be represented by ellipses 180, 185 and 190 of FIG. 1C. The location at which these ellipses intersect (point n,p) represents the true location of the scatterer. Beam forming hardware, firmware, or software can combine the echoes from each receive element to generate an image, effectively reinforcing the image at the intersection of the ellipses. In some embodiments, many more receiver elements than the three shown may be used in order to obtain a desirable signal-to-noise ratio for the image. FIG. 1C also illustrates MAUI electronics, which can comprise the MAUI electronics described above with reference to FIGS. 1A and 2.

A method of rendering the location of all of the scatterers in the target object, and thus forming a two dimensional cross section of the target object, will now be described with reference to multi-aperture ultrasound imaging system 300 of FIG. 3. FIG. 3 illustrates a grid of points to be imaged by apertures 302 and 304. A point on the grid is given the rectangular coordinates (i,j). The complete image will be a two dimensional array called "echo." In the grid of FIG. 3, mh is the maximum horizontal dimension of the array and mv is the maximum vertical dimension. FIG. 3 also illustrates MAUI electronics, which can comprise the MAUI electronics described above with reference to FIGS. 1A and 2.

In one embodiment, the following pseudo code may be used to accumulate all of the information to be gathered from a transmit pulse from one transmit element (e.g., one element of T1 ... Tn from aperture 302), and the consequent echoes received by one receive element (e.g., one element of R1 ... Rm from aperture 304) in the arrangement of FIG. 3.

```
for (i = 0; i < mh; i++){
    for (j = 0; j < mv; j++){
        compute distance a
        compute distance b
        compute time equivalent of a+b
        echo[ i ][ j ] = echo[i ][ j]+stored received echo at the computed time delay.
    }
}
```

The fixed delay is primarily the time from the transmit pulse until the first echoes are received. As will be discussed later, an increment can be added or subtracted to compensate for varying fat layers.

A complete two dimensional image may be formed by repeating this process for every receive element in aperture 304 (e.g., R1 ... Rm). In some embodiments, it is possible to implement this code in parallel hardware resulting in real time image formation.

Combining similar images resulting from pulses from other transmit elements will improve the quality (e.g., in terms of signal-to-noise ratio) of the image. In some embodiments, the combination of images may be performed by a simple summation of the single point source pulse images (e.g., coherent addition). Alternatively, the combination may involve taking the absolute value of each element of the single point source pulse images first before summation (e.g., incoherent addition). In some embodiments, the first technique (coherent addition) may be best used for improving lateral resolution, and the second technique (incoherent addition) may be best applied for the reduction of speckle noise. In addition, the incoherent technique may be used with less precision required in the measurement of the relative positions of the transmit and receive apertures. A combination of both techniques may be used to provide an optimum balance of improved lateral resolution and reduced speckle noise. Finally, in the case of coherent addition, the final sum should be replaced by the absolute value of each element, and in both cases, some form of compression of the dynamic range may be used so that both prominent features and more-subtle features appear on the same display. In some embodiments, additional pixel locations are located on a grid without scan-conversion.

In some embodiments, compression schemes may include taking the logarithm (e.g., $20 \log_{10}$ or "dB") of each element before display, or taking the nth root (e.g., $4^{th}$ root) of each element before display. Other compression schemes may also be employed.

Referring still to FIG. 3, any number of receive probes and transmit probes may be combined to enhance the image of scatterer (i,j) as long as the relative positions of the transducer elements are known to a designed degree of precision, and all of the elements are in the same scan plane and are focused to either transmit energy into the scan plane or receive energy propagated in the scan plane. Any element in any probe may be used for either transmit or receive or both.

The speed-of-sound in various soft tissues throughout the body can vary by +/–10%. Using typical ultrasound techniques, it is commonly assumed that the speed-of-sound is constant in the path between the transducer and the organ of interest. This assumption is valid for narrow transducer arrays in systems using one transducer array for both transmit and receive. However, the constant speed-of-sound assumption breaks down as the transducer's aperture becomes wider because the ultrasound pulses pass through more tissue and possibly diverse types of tissue, such as fat, muscle, blood vessels, etc. Tissue diversity under the width of the transducer array affects both the transmit and the receive functions.

When a scatterer is insonified by a point source pulse from a single transmit element, it reflects back an echo to all of the elements of the receiver group. Coherent addition of images collected by elements in this receive aperture can be effective if the speed-of-sound variations in the paths from scatterer (i,j) to each of the receiver elements do not exceed +–180 degrees phase shift relative to one path chosen as reference. Referring to FIG. 3, the maximum size of the receive aperture for which coherent addition can be effective is dependent on tissue variation within the patient and cannot be computed in advance. However, a practical maximum for a particular transmit frequency can be determined from experience.

When insonifying with unfocused point source pulses, the aperture size of the transmit group is not highly critical since variation in the path time from transmitter elements to a scatterer such as scatterer (i,j) will change only the displayed position of the point. For example, a variation resulting in a phase shift of 180 degrees in the receive paths results in complete phase cancellation when using coherent addition, whereas the same variation on the transmit paths results in a displayed position error of only a half wavelength (typically about 0.2 mm), a distortion that would not be noticed.

Thus, in a multi-aperture imaging system with one aperture used only for transmit and the other used only for receive during a single transmit/receive cycle, as is illustrated in FIG. 1A, very little additional compensation for the speed-of-sound variation is needed. Although the aperture has been increased from element T1 to Rm which can be many times the width of a conventional sector scanner probe, the concern of destructive interference of the signals from scatterer (i,j) is independent of the width of the transmit aperture or the separation of the apertures, and is dependent only on the width of the receive aperture (element R1 to Rm). The standard width for which speed-of-sound variation presents a minimal problem in practice is about 16-20 mm for 3.5 MHz systems (and smaller for higher frequencies). Therefore, no explicit compensation for speed-of-sound variation is necessary if the receive aperture has the same or smaller width than standard apertures.

Substantial improvement in lateral resolution is achieved with a receive aperture of the same width as a conventional single array 1D, 1.5D or 2D ultrasound probe used for both transmit and receive, because received energy when imaging adjacent cells (i.e., regions of the target object) to that which represents a scatterer is dependent on the time difference between when an echo is expected to arrive and the time that it actually arrives. When the transmit pulse originates from the same array used for receive, the time difference is small. However, when the transmit pulse originates from a second array at some distance from the receive array, the time difference is larger and therefore more out of phase with the signal for the correct cell. The result is that fewer adjacent cells will have signals sufficiently in phase to falsely represent the true scatterer.

Figure 4:
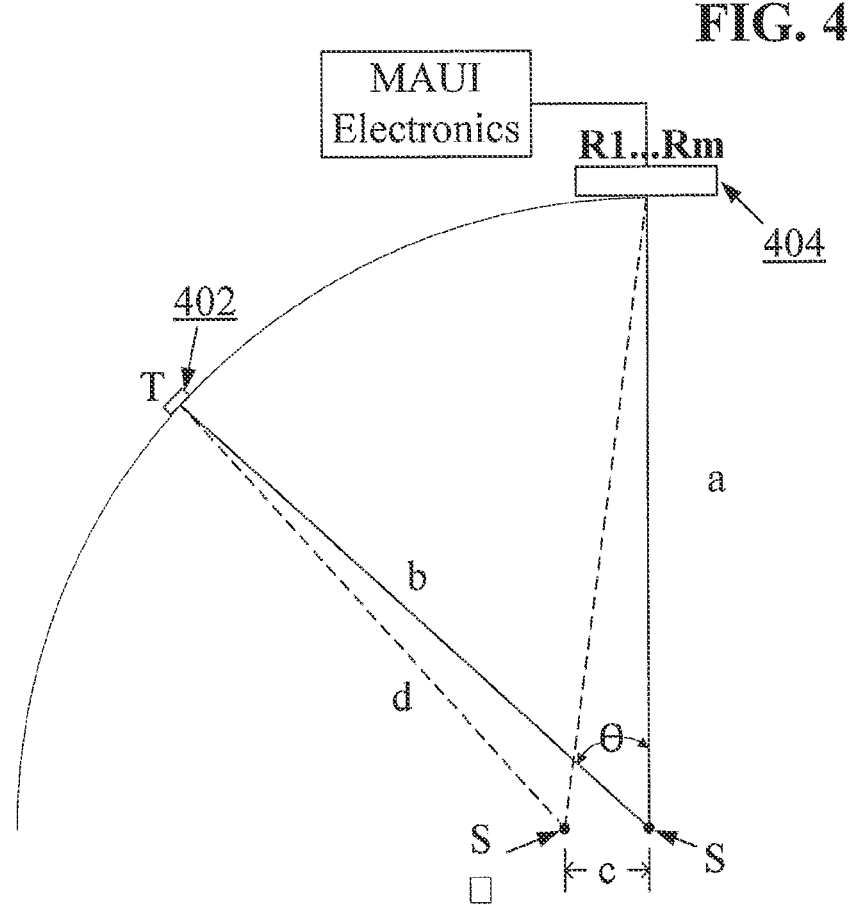
FIG. 4: Fat layer model with a three-aperture system.

Referring to FIG. 4, consider the signal received at a single element (e.g., one of receive elements R1 . . . Rm) of a receive aperture 404 from a scatterer at "S". If both the transmit and receive functions are performed on the same element, the time for the ultrasound to propagate to "S" and be returned would be 2a/C (where C is the speed-of-sound in tissue). When the reconstruction algorithm is evaluating the signal received for a possible scatterer in an adjacent cell "S'" separated "c" distance from the true scatterer, "S", the expected time of arrival is $2(sqrt(a^2+c^2)/C)$. When "c" is small, this time is almost the same and so the signal from "S" will be degraded only slightly when estimating the magnitude of the scatterer "S'" in the adjacent cell. FIG. 4 also illustrates MAUI electronics, which can comprise the MAUI electronics described above.

Now consider moving the transmitting aperture 402 away from the receive aperture 404 by an angle theta ("θ"). For convenience in comparison, let the distance "b" from aperture 402 to scatterer "S" be equal to the distance "a" from aperture 404 to scatterer "S". The time for the ultrasound to propagate from the transmit aperture 402 to "S" and be returned to the receive aperture 404 would still be $(a+b)/C=2a/C$ (with a=b), but the expected time for the signal to propagate to the adjacent cell "S'" would be $(d+sqrt(a^2+c^2))/C=(sqrt((a \sin θ-c)^2+(a \cos θ)^2)+sqrt(a^2+c^2))/C$. The difference between the expected time of arrival and actual would then be $Diff=(sqrt((a \sin θ-c)^2+(a \cos θ)^2)+sqrt(a^2+c^2)-2a)/C$.

To put some numbers in this equation, suppose that the separation of aperture 402 and aperture 404 is only 5 degrees, distance a=400 cells, and distance c=1 cell. Then the ratio of the difference in time-of-arrival for θ=5 degrees to that for θ=0 degrees is 33.8. That is, the drop off of display amplitude to adjacent cells is 33 times faster with θ=5 degrees. The larger difference in time-of-arrival greatly simplifies the ability to uniquely distinguish echo information from adjacent cells. Therefore, with high theta angles, the display of a point will be less visible as noise in adjacent cells and the result will be higher resolution of the real image. With multiple aperture transmitters and receivers, we can make the angle as high as needed to improve resolution.

Simulation for a realistic ultrasound system with multiple reflectors in multiple cells shows that the effect is still significant, but not as dramatic as above. For a system comprising a receive aperture of 63 elements, a θ of 10 degrees, and a transmit pulse from a point-source transmit aperture that extends for 5 cycles with cosine modulation, the lateral spread of the point spread function was improved by a factor of 2.3.

Explicit Compensation for Speed-of-Sound Variation

A single image may be formed by coherent averaging of all of the signals arriving at the receiver elements as a result of a single point source pulse for insonification. Summation of these images resulting from multiple point source pulses can be accomplished either by coherent addition, incoherent addition, or a combination of coherent addition by groups and incoherent addition of the images from the groups. Coherent addition (retaining the phase information before addition) maximizes resolution whereas incoherent addition (using the magnitude of the signals and not the phase) minimizes the effects of registration errors and averages out speckle noise. Some combination of the two modes may be preferred. Coherent addition can be used to average point source pulse images resulting from transmit elements that are close together and therefore producing pulses transmitted through very similar tissue layers. Incoherent addition can then be used where phase cancellation would be a problem. In the extreme case of transmission time variation due to speed-of-sound variations, 2D image correlation can be used to align images prior to addition.

When an ultrasound imaging system includes a second aperture, using the second aperture for receiving as well as transmitting produces much better resolution. In combining the images from two or more receive arrays; it is possible and beneficial to use explicit compensation for the speed-of-sound variation.

Figure 5:
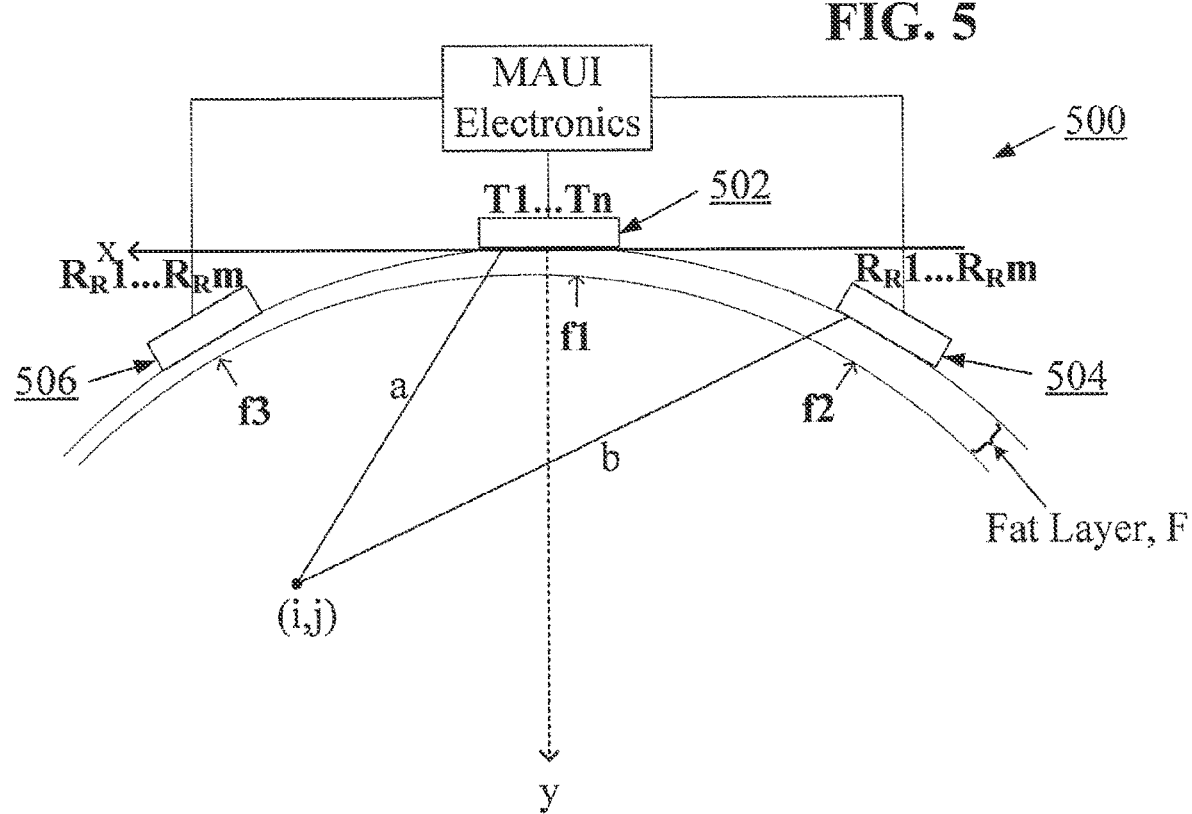
FIG. 5: Construction for estimation of point spread function.

Consider the tissue layer model for the three-aperture ultrasound imaging system 500 as shown in FIG. 5, which illustrates the effects of varying thicknesses of different types of tissue, such as fat or muscle. A fat layer "F" is shown in FIG. 5, and the thickness of the tissue layers f1, f2, and f3 under each aperture 502, 504, and 506, respectively, is different and unknown. It is not reasonable to assume that the tissue layer at aperture 506 will be the same as at aperture 504, and so coherent addition of the signals from all of the receive elements together is not usually possible. In one example, if the tissue layer at aperture 504 were as much as 3 cm larger than that at aperture 506, this corresponds to about 3 wavelengths (at 3.5 MHz) displacement of the signals, but this is only 1.3 mm displacement of the representation of the deep tissues. For such small displacements, only a tiny amount of geometric distortion of the image would be observed. Therefore, although coherent addition is not possible, incoherent addition with displacement of one image relative to the other is possible.

Image comparison techniques may be used to determine the amount of displacement needed to align image frames from left and right apertures (e.g., apertures 506 and 504, respectively). In one embodiment, the image comparison technique can be cross-correlation. Cross-correlation involves evaluating the similarity of images or image sections to identify areas with a high degree of similarity. Areas with at least a threshold value of similarity may be assumed to be the same. Thus, by identifying areas within images with high degrees of similarity, one image (or a section thereof) may be shifted such that areas with substantial similarity overlap and enhance overall image quality. FIG. 5 also illustrates MAUI electronics, which can comprise the MAUI electronics described above.

Further, these image comparison techniques can also be used by applying sub-image analysis, which can be used to determine displacement of sub-images and accommodate for localized variation in speed-of-sound in the underlying tissue. In other words, by breaking down the images into smaller segments (e.g., halves, thirds, quarters, etc.), small portions of a first image may be compared to the corresponding small portion of a second image. The two images may then be combined by warping to assure alignment. Warping is a technique understood by those skilled in the art, and is described, for example in U.S. Pat. No. 7,269,299 to Schroeder.

The same technique of incoherent addition of images from multiple receive transducer arrays may be applied to any number of apertures. The same idea may be applied even to a single element array which is too wide to be used for coherent addition all at once. An ultrasound imaging system with a single wide array of elements may be divided into sections (apertures) each of which is small enough for coherent addition, and then the images resulting from these sections may be combined incoherently (with displacement if necessary).

Even a slight distortion of the image may be compensated for with sufficient computational power. Image renderings may be computed for one receive array using varying amounts of delay in the rendering algorithm (echo[i][j]= echo[i][j]+stored receive echo at the computed time+delay). Then the best matched of these (by cross-correlation or some other measure of acuity) may be incoherently added to the image from the other receive array(s). A faster technique includes calculating the cross correlation network for the uncorrected pair of images, and feeding this into a neural network trained to pick the correction delay.

Because multiple aperture ultrasound systems that can correct for speed of sound incongruences allow for significantly larger apertures, some embodiments of the multi-aperture ultrasound systems described herein can have apertures located 10 cm apart from one another. Since resolution is proportional to $2\lambda/D$, this larger aperture leads to higher resolution of tissues located well below the surface of the skin. For instance, the renal arteries are frequently located 10 cm to 15 cm below the skin and are 4 mm to 6 mm in size near the abdominal aorta. Phased array, linear array and synthetic aperture ultrasound systems usually cannot detect this physiology in most patients; specifically because the aperture size is not large enough to have adequate lateral resolution. Typically, phased array systems have aperture sizes of approximately 2 cm. Increasing the aperture size from larger than 2 cm to approximately 10 cm in a multi-aperture ultrasound system can increase the resolution by up to 5×.

3D Imaging

In some embodiments, three-dimensional information may be obtained by moving a two-dimensional imaging system and acquiring 2D slices at a number of positions or angles. From this information and using interpolation techniques, a 3D image at any position or angle may be reconstructed. Alternatively, a 2D projection of all of the data in the 3D volume may be produced. A third alternative is to use the information in a direct 3D display.

Because multi-aperture ultrasound imaging systems may result in wider probe devices, the easiest way to use them to obtain 3D data is to not move them on the patient's skin but merely rock them so that the 2D slices span the 3D volume to be imaged. In some embodiments, a mechanical rotator mechanism which records position data may be used to assist in the collection the 2D slices. In other embodiments, a freely operated ultrasound probe with precision position sensors (such as gyroscopic sensors) located in the head of the probe may be used instead. Such an apparatus allows for complete freedom of movement while collecting 2D slices. Finally, intravenous and intracavity probes may also be manufactured to accommodate wide apertures. Such probes may be manipulated in similar ways in order to collect 2D slices.

This combination is particularly desirable for 3D cardiac imaging using a multi-aperture ultrasound imaging system. Most patients have good acoustic windows in two intercostal spaces next to the sternum. A multi-aperture imaging system is ideal in this case since the intervening rib would render a flat probe useless, while a probe with at least two widely spaced apertures can be positioned such that a send aperture and a receive aperture align with separate intercostal spaces. Once a probe with multiple apertures is in place, it cannot be rotated, but it can be rocked to obtain the 3D information. A multi-aperture probe may also be used in the same intercostal space but across the sternum.

3D information may also be obtained directly with multi-aperture imaging systems having apertures that are not all in the same scan plane. In this case the elements making up the transmit aperture preferably propagate spherical waveforms (rather than circular waveforms confined to one plane of scan). The elements making up the receive apertures may likewise be sensitive to energy arriving from all directions (rather than being sensitive only to ultrasonic energy in a single plane of scan). The reconstruction pseudo code provided above may then be extended to three dimensions.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. An ultrasound probe, comprising:
a probe body housing a transducer array comprising a plurality of transducers arranged in a concave shape, the transducer array being configured to transmit unfocused two-dimensional ultrasound waveforms into tissue;
one or more precision position sensors located in the probe body, the precision position sensors being configured to record position information during transmission of the unfocused two-dimensional ultrasound waveforms;
at least one processor configured to establish a transmit aperture of the transducer array spaced apart from a receive aperture of the transducer array, wherein the transmit aperture and receive aperture are not in a common scan plane, the at least one processor being further configured to generate 3D ultrasound imaging datasets based on the unfocused two-dimensional ultrasound waveforms and the position information.

2. The ultrasound probe of claim 1, wherein the 3D ultrasound imaging datasets are produced by rocking the probe body on a patient's skin.

3. The ultrasound probe of claim 1, wherein the at least one processor is configured to correct for speed of sound incongruences in the tissue.

4. The ultrasound probe of claim 1, wherein the transmit aperture and the receive aperture are separated by a distance of 10 cm or greater.

5. The ultrasound probe of claim 1, wherein the at least one processor is configured to increase an angle between the transmit aperture and the receive aperture to improve resolution.

* * * * *